(12) United States Patent
Kellinger

(10) Patent No.: US 10,287,560 B2
(45) Date of Patent: May 14, 2019

(54) RECOMBINASE MUTANTS

(71) Applicant: Illumina, Inc., San Diego, CA (US)

(72) Inventor: Matthew William Kellinger, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 15/471,169

(22) Filed: Mar. 28, 2017

(65) Prior Publication Data

US 2017/0275601 A1 Sep. 28, 2017

Related U.S. Application Data

(60) Provisional application No. 62/314,273, filed on Mar. 28, 2016.

(51) Int. Cl.
*C12N 9/12* (2006.01)
*C12N 9/00* (2006.01)

(52) U.S. Cl.
CPC ............ *C12N 9/1241* (2013.01); *C12N 9/00* (2013.01); *C12Y 207/07* (2013.01); *C12N 2795/10122* (2013.01)

(58) Field of Classification Search
None
See application file for complete search history.

(56) References Cited

U.S. PATENT DOCUMENTS

| | | | |
|---|---|---|---|
| 5,223,414 A | 6/1993 | Zarling et al. | |
| 7,270,981 B2 | 9/2007 | Armes et al. | |
| 7,399,590 B2 | 7/2008 | Piepenburg et al. | |
| 7,435,561 B2 | 10/2008 | Piepenburg et al. | |
| 7,485,428 B2 | 2/2009 | Armes et al. | |
| 7,666,598 B2 | 2/2010 | Piepenburg et al. | |
| 7,742,463 B2 | 6/2010 | Lam et al. | |
| 7,763,427 B2 | 7/2010 | Piepenburg et al. | |
| 8,017,399 B2 | 9/2011 | Jarvis et al. | |
| 8,030,000 B2 | 10/2011 | Piepenburg et al. | |
| 8,062,850 B2 | 11/2011 | Piepenburg et al. | |
| 8,071,308 B2 | 12/2011 | Piepenburg et al. | |
| 8,563,748 B2 | 10/2013 | Korte et al. | |
| 8,637,253 B2 | 1/2014 | Piepenburg et al. | |
| 2009/0029421 A1 | 1/2009 | Piepenburg et al. | |
| 2013/0338042 A1 | 12/2013 | Shen et al. | |
| 2016/0090581 A1 | 3/2016 | Bomati et al. | |
| 2016/0326502 A1 | 11/2016 | Piepenburg et al. | |

FOREIGN PATENT DOCUMENTS

| | | |
|---|---|---|
| CN | 105 349 696 A | 2/2016 |
| CN | 105349696 A | 2/2016 |
| WO | WO 2008/035205 A2 | 3/2008 |
| WO | WO2008/035205 A2 | 3/2008 |
| WO | WO 2010/141940 A1 | 12/2010 |
| WO | WO2010/141940 A1 | 12/2010 |
| WO | WO 2012/138989 A1 | 10/2012 |
| WO | WO2012/138989 A1 | 10/2012 |
| WO | WO 2013/188582 A1 | 12/2013 |
| WO | WO 2016/054088 A1 | 4/2016 |
| WO | WO2016/054088 A1 | 4/2016 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Guo et al. (H. Guo et al., "Protein Tolerance to Random Amino Acid Change", PNAS 101(25): 9205-9210, Jun. 2004.*
Altschul et al., "Basic local alignment search tool," *J. Mol. Biol.*, Oct. 5, 1990; 215(3):403-410.
Arnold, "Protein engineering for unusual environments," *Current Opinion in Biotechnology*, 1993; 4:450-455.
Bass et al., "Mutant Trp repressors with new DNA-binding specificities," *Science*, 1988; 242:240-245.
Bell, "Structure and mechanism of *Escherichia coli* RecA ATPase", Sep. 19, 2005, *Molecular Microbiology*, 58(2):358-366.
Bianco et al., "DNA Strand Exchange Proteins: A Biochemical and Physical Comparison", Jun. 17, 1998, *Frontiers in Bioscience*, 3:d570-603.
Bordo and Argos, "Suggestions for "Safe" Residue Substitutions in Site-directed Mutagenesis," *J.Mol. Biol.*, Feb. 20, 1991; 217(4):721-729.
Botstein and Shortle, "Strategies and applications of in vitro mutagenesis," *Science*, Sep. 20, 1985; 229(4719):1193-1201.
Carter et al., "Improved oligonucleotide site-directed mutagenesis using M13 vectors," *Nucl. Acids Res.*, Jun. 25, 1985; 13(12):4431-4443.
Carter, "Site-directed mutagenesis," *Biochem. J.*, 1986; 237(1):1-7.
Carter, "Improved oligonucleotide-directed mutagenesis using M13 vectors," *Methods in Enzymol*, 1987; 154:382-403.
Clackson et al., "Making antibody fragments using phage display libraries," *Nature*, Aug. 15, 1991; 352:624-628.
Crameri et al., "DNA shuffling of a family of genes from diverse species accelerates directed evolution," *Nature*, Jan. 15, 1998; 391:288-291.
Dale and Belfield, "Oligonucleotide-directed random mutagenesis using the phosphorothioate method," *Methods in Molecular Medicine*, 1996; 57:369-374.
Database UniPort [Online], XP-002770704, Database accession No. A0A023W4N6 sequence, Jul. 9, 2014; 1 page.
Eghtedarzadeh and Henikoff, "Use of oligonucleotides to generate large deletions," *Nucl. Acids Res.*, Jun. 1986; 14(12):5115.
Farb et al., "Role of Allosteric Switch Residue Histidine 195 in Maintaining Active-Site Asymmetry in Presynaptic Filaments of Bacteriophage T4 UvsX Recombinase," *Journal of Molecular Biology*; Jan. 16, 2009; 385(2):393-404.

(Continued)

Primary Examiner — Richard G Hutson
(74) Attorney, Agent, or Firm — Mueting, Raasch & Gebhardt, P.A.

(57) ABSTRACT

Presented herein are recombinases for improved recombinase-mediated amplification of nucleic acids, such as a PCR-library having single-stranded adapter regions, on a patterned flow cell surface for improved cluster amplifications, as well as methods and kits using the same.

20 Claims, 4 Drawing Sheets

Specification includes a Sequence Listing.

(56) References Cited

OTHER PUBLICATIONS

Fritz et al., "Oligonucleotide-directed construction of mutations: a gapped duplex DNA procedure without enzymatic reactions in vitro," *Nucl. Acids Res.*, Jul. 25, 1988; 16(14B):6987-6999.
Gajewski et al., "Crystal Structure of the Phage T4 Recombinase UvsX and Its Functional Interaction with the T4 SF2 Helicase UvsW," *Journal of Molecular Biology*, Jan. 7, 2011; 405(1):65-76.
Gibbs et al., "Degenerate oligonucleotide gene shuffling (DOGS): a method for enhancing the frequency of recombination with family shuffling," *Gene*, 2001; 271:13-20.
Grundstrom et al., "Oligonucleotide-directed mutagenesis by microscale 'shot-gun' gene synthesis," *Nucl. Acids Res.*, May 10, 1985; 13(9):3305-3316.
Hayes et al., "Combining Computational and Experimental Screening for rapid Optimization of Protein Properties," *PNAS*, Dec. 10, 2002; 99(25):15926-15931.
Henikoff and Henikoff, "Amino acid substitution matrices from protein blocks," *Proc. Natl. Acad. Sci. USA*, Nov. 1992; 89:10915-10919.
Hiraga and Arnold, "General method for sequence-independent site-directed chimeragenesis," *J. Mol. Biol.*, Jul. 4, 2003; 330(2):287-296.
Karlin and Altschul, "Applications and statistics for multiple high-scoring segments in molecular sequences," *Proc. Natl. Acad. Sci. USA*, Jun. 15, 1993; 90(12):5873-7.
Kramer et al., "The gapped duplex DNA approach to oligonucleotide-directed mutation construction," *Nucl. Acids Res.*, Nov. 22, 1984; 12(24):9441-9456.
Kramer and Fritz, "Oligonucleotide-directed construction of mutations via gapped duplex DNA," *Methods in Enzymol.*, 1987; 154:350-367.
Kramer et al., "Different Base/Base Mismatches Are Corrected with Different Efficiencies by the Methyl-Directed DNA Mismatch-Repair System of *E. coli*," *Cell*, Oct. 1984; 38:879-887.
Kramer et al., "Improved enzymatic in vitro reactions in the gapped duplex DNA approach to oligonucleotide-directed construction of mutations," *Nucl. Acids Res.*, Jul. 25, 1988; 16(14B):7207.
Kunkel, "Rapid and efficient site-specific mutagenesis without phenotypic selection," *PNAS*, Jan. 1985; 82(2):488-492.
Kunkel et al., "Rapid and efficient site-specific mutagenesis without phenotypic selection," *Methods in Enzymol.*, 1987; 154:367-382.
Ling et al., "Approaches to DNA mutagenesis: an overview," *Anal. Biochem.*, Dec. 15, 1997; 254(2):157-178.
Liu et al., "Assembly and dynamics of the bacteriophage T4 homologous recombination machinery", 2010, *Virology Journal*, 7(357): 1-15.
Lorimer and Pastan, "Random recombination of antibody single chain Fv sequences after fragmentation with DNaseI in the presence of Mn2+," *Nucleic Acids Res.*, Aug. 11, 1995; 23(15):3067-3068.
Maher et al., "Coordinated Binding of Single-Stranded and Double-Stranded DNA by UvsX Recombinase", 2013, *PLOS One*, 8(6): e66654, 1-11.
Mandecki, "Oligonucleotide-directed double-strand break repair in plasmids of *Escherichia coli*: a method for site-specific mutagenesis," *Proc. Natl. Acad. Sci. USA*, Oct. 1986; 83:7177-7181.
Nakamaye and Eckstein, "Inhibition of restriction endonuclease NciI cleavage by phosphorothioate groups and its application to oligonucleotide-directed mutagenesis," *Nucl. Acids Res.*, Dec. 22, 1986; 14(24):9679-9698.
Nambiar et al., "Total synthesis and cloning of a gene coding for the ribonuclease S protein," *Science*, Mar. 23, 1984; 223(4642):1299-1301.
Needleman and Wunsch, "A general method applicable to the search for similarities in the amino acid sequence of two proteins," *J. Mol. Biol.*, Mar. 1970; 48(3):443-453.
Pearson and Lipman, "Improved tools for biological sequence comparison," *Proc. Nat'l. Acad. Sci. USA*, Apr. 1988; 85(8):2444-2448.
Previte et al., "DNA sequencing using polymerase substrate-binding kinetics," *Nature Communications*, Jan. 23, 2015; 6(5936):1-12.
Sakamar and Khorana, "Total synthesis and expression of a gene for the a-subunit of bovine rod outer segment guanine nucleotide-binding protein (transducin)," *Nucl. Acids Res.*, Jul. 25, 1988; 16(14A):6361-6372.
Sayers et al., "5'-3' Exonucleases in phosphorothioate-based oligo-nucleotide-directed mutagenesis," *Nucl. Acids Res.*, Feb. 11, 1988; 16(3):791-802.
Sayers et al., "Strand specific cleavage of phosphorothioate-containing DNA by reaction with restriction endonucleases in the presence of ethidium bromide," *Nucl. Acids Res.*, Feb. 11, 1988; 16(3):803-814.
Sieber, et al., "Libraries of hybrid proteins from distantly related sequences," *Nature Biotechnology*, May 2001; 19(5):456-460.
Smith and Waterman, "Comparison of biosequences," *Adv. Appl. Math.*, Dec. 1981; 2(4):482-489.
Smith, "In vitro mutagenesis," *Ann. Rev. Genet.*, 1985; 19:423-462.
Stefanska et al., "Discovery and characterization of RecA protein of thermophilic bacterium *Thermus thermophilus*MAT72 phage Tt72 that increases specificity of a PCR-based DNA amplification," *Journal of Biotechnology*, Apr. 28, 2014; 182:1-10.
Stemmer, "Rapid evolution of a protein in vitro by DNA shuffling," *Nature*, Aug. 4, 1994; 370:389-91.
Taylor et al., "The use of phosphorothioate-modified DNA in restriction enzyme reactions to prepare nicked DNA," *Nucl. Acids Res.*, Dec. 20, 1985; 13(24):8749-8764.
Taylor et al., "The rapid generation of oligonucleotide-directed mutations at high frequency using phosphorothioate-modified DNA," *Nucl. Acids Res.*, Dec. 20, 1985; 13(24):8765-8787.
Wells et al., "Importance of hydrogen-bond formation in stabilizing the transition state of subtilisin," *Phil. Trans. R. Soc. Lond.*, Apr. 1986; A 317: 415-423.
Wells et al., "Cassette mutagenesis: an efficient method for generation of multiple mutations at defined sites," *Gene*, 1985; 34(2-3):315-323.
Zoller and Smith, "Oligonucleotide-directed mutagenesis using M13-derived vectors: an efficient and general procedure for the production of point mutations in any DNA fragment," *Nucleic Acids Res.*, Aug. 6, 1982; 10(20):6487-6500.
Zoller and Smith, "Oligonucleotide-directed mutagenesis of DNA fragments cloned into M13 vectors," *Methods in Enzymol.*, 1983; 100:468-500.
Zoller and Smith, "Oligonucleotide-directed mutagenesis: a simple method using two oligonucleotide primers and a single-stranded DNA template," *Methods in Enzymol.*, 1987; 154:329-350.
International Search Report and Written Opinion dated Jul. 5, 2017, in related application PCT/US2017/024451. 19 pages.
PCT International Search Report and Written Opinion for PCT/US2017/024451.
International Preliminary Report on Patentability dated Oct. 11, 2018, in related application PCT/US2017/024451, 12 pages.

\* cited by examiner

FIG. 1A

ALIGNMENT OF UvsX RELATIVES

```
t4        MYSADTVFIIGKRQIKDGSDLQGYQFVLNVEKSRTVKEKSKFFIDVKFD-GGIDPYSGLL
t6        MYSADTVFIIGKRQIKDGSDLQGYQFVLNVEKSRTVKEKSKFFIDVKFD-GGIDPYSGLL
Phage133  MYSADTVFFIGKRQVKDGTELAGYEFILKAEKSEMVKEKSVFPITVKFD-GGIDPYSGLL
Rb69      LYSANTVFFISKRQVKEGTELIGYDPTLKAEKSRTVKEKSTFPITVNFD-GGIDPFSGLL
Aeh1      TYSSDTVIIIGRQQEKDGKELLGYNFVLNMEKSRFVKEQSKLPLEVTFQ-GGINTYSGML
Ae65      MYSADTVIILGKQQDKDGKELLGYNPVMNAEKSRAIKEKSKLDLMVSFE-GGINTYSGLL
Kvp40     MYSADTVIILGKQQEKDGKDIIGYHFIMNIEKSRFVKEKMKVPLTVTYE-NGIDPFSGLL
Rb43      MYSADTAIILGKQQVKEGTEVVGYDFIMNIEKSRPVKEKSKFPLHVTYE-GGISMYSGLL
PSSM2     KYAASTIIYLSKKKEKDQKEVIGNLIKAKTHKSRLSKENKEVQIRLYYDERGLDRYYGLL
PSSM4     KYAASTIVYLSKKKEKNGKEVVGNIIKCKTAKSRLTKENSDVETRLYYD-RGLDRYYGLL
          *:.,*  , :,::: *: ,:: *   :  :  *  :   :  : *:, : *:* t4        DMALELGFVVKPKNGWYAREFLDEETGEMI--REEEKWRAKDTNCTTFWGHLFKHQPFRD
t6        DMALELGFVVKPKNGWYAREFLDEETGEMI--REEEKWRAKDTNCTTFWGHLFKHQPFRD
Phage133  EMATDLGFVVKPKVGWYKRAMMVD--GVMQ--HEEEKSWRAKDTDSIDFWGHLFKHDEFRK
Rb69      EMATEIGFVVKPKAGWYAREFLDEETGEMI--REEEKSWRAKATDCVEFWGHLFKHKPFRD
Aeh1      DIALEVGFVVKPSNGWFSRAFLDEETGELV--ERDFKWRRADTNCLEFWKHMFAHQPFKT
Ae65      KIAQELGFVTKPQNARYQRNFLDLEPGEMVIPEDEFKWTEEESDSLEFWKHMFSHKPFMD
Kvp40     DIALQTGHVVKPSNGWYQRATVDEETGEMI--VEEFKYRAKETQTISFWKHIINSPTFKE
Rb43      DLAMEMNFVQTPTXGWRGRAFLNTETGELE--LEEFKWRESETNSIEFWRHLFTRQPFLD
PSSM2     ELG-EIGGMWKNVAGRYEMNGXKIYAKEIL--KNPTEYFTDDI-------H--MEQLDN
PSSM4     ELG-EKHGVFSRKGNRVVVGDSSVYPSAIL--ADPEKYFTEEL-------H--MEKLDE
          .:,     .:        :          :   :   ,:

t4        AIKRAYQLGAIDSNEIVEAEVDELINSKVEKFKSP--ESKSKSAADLETDLEQLSDMEEF
t6        AIKRAYQLGAIDSNEIVEAEVDELINSKVEKFKSP--ESKSKSAADLETDLEQLSDMEEF
Phage133  AIERYQLGSIESDAEVDAEVDALIGSKTTAKISGVNFGPAESAADKEQQLEDPVD----
Rb69      AIETKYKLGAISSIKEVDDAVEDLINCKATTKV-PVKTSDAPSAADIENDLDEMED---F
Aeh1      ACSDMFKLKSVAVKDEVFDEVDELFSGEAEMPVNMGRKLDTADQEEIDQLEEVDVEGSDS
Ae65      AVSHAYKLKAVEVSQEVFDEVDQLPG----------------------------------
Kvp40     GVKRIYCLGQLD-ESELPGEVDSLFD----------------------------------
Rb43      AIQDKYRIPDKEITDG--AALEDLYSTDEPESNKIDLDDDIPDDIGIDQDEEPIM-----
PSSM2     IAKEHPSYGTN-------------------------------------------------
PSSM4     AAAKEFRYGN-------------------------------------------------- t4        NE------
t6        NE------
Phage133  ED------
Rb69      DE------
Aeh1      DELFANLD
Ae65      --------
Kvp40     --------
Rb43      --------
PSSM2     --------
PSSM4     --------
```

FIG. 1B

```
RB49    MS-VLEKLKKNSTLKTTAVLSKSSFFNEKTNTRTKIPMLNIAFSGDLKKGFQSGLIFFAGPSKHFK   65
T4      MSDLKSRLIKASTSKLTAELTASKFFNEKDVVRTKIPMMNIALSGEITGGMQSGLLILAGPSKSFK   66

RB49    SNMGLTCVSAYMKQNPDAACLFFDSEFGITSAYLESMGVDPDRVVHVPIKNIEELKFEIM        125
T4      SNFGLTMVSSYMRQYPDAVCLFYDSEFGITPAYLRSMGVDPERVIHTPVQSLEQLRIDMV        126

RB49    NQLEQITREDKVIIFIDSIGNLASKKEVEDAINEKSAQDMTRAKALKGLFRMVTPYLTMN        185
T4      NQLDAIERGEKVVVFIDSLGNLASKKETEDALNEKVVSDMTRAKTMKSLFRIVTPYFSTK        186

RB49    DIPCIAINHTYETQEMFSKTVMSGGTGAMYSANEVFIIGREQQKEGTEITGYDFILNAEK        245
T4      NIPCIAINHTYETQEMFSKTVMGGGTGPMYSADTVFIIGKEQIKDGSDLQGYQFVLNVEK        246

RB49    SRTVKEKSKF#ISVTFSGGIDPYSGLLELAVELGWVVKPSNGWYSRSILNTETGEMETEE       305
T4      SRTVKEKSKF#IDVKFDGGIDPYSGLLDMALELGFVVKPKNGWYAREFLDEETGEMIREE       306
                  ▼                    ▼
RB49    RKFRAKETNSIEFWKPLLTNDKFNEAINDHYKLGQVISDEAVDKEIEDML       355
T4      KSWRAKDTNCTTFWGPLFKHQPFRDAIKRAYQLGAIDSNEIVEAEVDELI       356
```

FIG. 2

RECOMBINASE MUTANTS

CONTINUING APPLICATION DATA

This application claims the benefit of U.S. Provisional Application Ser. No. 62/314,273, filed Mar. 28, 2016, which is incorporated by reference herein in its entirety.

SEQUENCE LISTING

This application contains a Sequence Listing electronically submitted to the United States Patent and Trademark Office via EFS-Web as an ASCII text file entitled "1447 SeqLisiting_ST25," having a size of 97.7 kilobytes and created on Mar. 24, 2017. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

BACKGROUND

Recombinase enzymes are useful in recombinase-mediated amplification of nucleic acids. For example, recombinase enzymes can facilitate targeting of oligonucleotides to DNA targets allow replication of DNA by a polymerase. There remains a need for modified recombinases with improved properties.

BRIEF SUMMARY

Presented herein are recombinases for improved recombinase-mediated amplification of nucleic acids. The present inventors have surprisingly identified certain altered recombinases which have substantially improved characteristics in the seeding nucleic acids onto a patterned flow cell surface. In certain embodiments, the altered recombinases of improve seeding a PCR-free library, such as a PCR-library having single-stranded adapter regions, on a patterned flow cell surface for improved cluster amplification.

The present invention includes an altered UvsX recombinase having an amino acid sequence that is at least 60%, 70%, 80%, 90%, 95%, or 99% identical to SEQ ID NO: 1, which recombinant UvsX includes at least one amino acid substitution mutation at the positions functionally equivalent to Pro321 and Asp334 in the RB49 UvsX amino acid sequence.

In some aspects, the at least one substitution mutation includes a mutation to a charged residue.

In some aspects, the at least one substitution mutation includes a mutation to a basic residue.

In some aspects, the at least one substitution mutation includes a mutation homologous to Pro321Lys in the RB49 UvsX amino acid sequence.

In some aspects, the at least one substitution mutation includes a mutation homologous to Asp334Lys in the RB49 UvsX amino acid sequence.

In some aspects, the at least one substitution mutation includes mutations homologous to Pro321Lys and Asp334Lys in the RB49 UvsX amino acid sequence.

In some aspects, an altered recombinase includes any of the recombinant UvsX recombinases discussed above, further having a substitution mutation at a position functionally equivalent to Pro256 in the RB49 UvsX amino acid sequence. In some aspects, a substitution mutation includes a mutation homologous to Pro256Lys in the RB49 UvsX amino acid sequence.

In some aspects, an altered recombinase includes any of the recombinant UvsX recombinases discussed above, further having a substitution mutation at a position functionally equivalent to His63 in the RB49 UvsX amino acid sequence. In some aspects, a substitution mutation includes a mutation homologous to His63Ser in the RB49 UvsX amino acid sequence.

In some aspects, an altered recombinase includes any of the recombinant UvsX recombinases discussed above, which is derived from a myoviridae phage selected from T4 (SEQ ID NO: 8), T6 (SEQ ID NO: 9), Rb69 (SEQ ID NO: 11), Aeh1 (SEQ ID NO: 12), KVP40 (SEQ ID NO: 14), *Acinetobacter* phage 133 (SEQ ID NO: 10), *Aeromonas* phage 65 (SEQ ID NO: 13), cyanophage P-SSM2 (SEQ ID NO: 16), cyanophage PSSM4 (SEQ ID NO: 17), cyanophage S-PM2 (SEQ ID NO: 18), Rb32 (SEQ ID NO: 19), *Vibrio* phage nt-1 (SEQ ID NO: 20), Rb16 (SEQ ID NO: 21), Rb43 (SEQ ID NO: 15), and Rb49 (SEQ ID NO: 1).

The present invention includes an altered UvsX recombinase having a substitution mutation to the semi-conserved domain comprising the amino acid sequence of any of SEQ ID NOs: 3-4, wherein the substitution mutation comprises a mutation selected from a substitution at position 4 to any residue other than Phe or Asp and/or having a substitution mutation to the semi-conserved domain comprising the amino acid sequence of any of SEQ ID NOs: 5-6, wherein the substitution mutation comprises a mutation selected from a substitution at position 4 to any residue other than Arg or Asp. In some aspects, the mutation includes a mutation to a charged residue. In some aspects, the mutation includes a substitution at position 4 to Lys.

The present invention includes an altered UvsX recombinase having the amino acid sequence of any one of SEQ ID NOs: 1, 2 and 8-35. In some aspects, the recombinant UvsX recombinase further includes a substitution mutation at a position functionally equivalent to Pro256 in the RB49 UvsX amino acid sequence, a substitution mutation at a position functionally equivalent to His63 in the RB49 UvsX amino acid sequence, a substitution mutation at a position functionally equivalent to Pro321 in the RB49 UvsX amino acid sequence, a substitution mutation at a position functionally equivalent to Asp334 in the RB49 UvsX amino acid sequence, and/or substitution mutations at positions functionally equivalent to Pro321 and Asp334 in the RB49 UvsX amino acid sequence. In some aspects, a substitution mutation includes a substitution mutation homologous to Pro256Lys in the RB49 UvsX amino acid sequence, a substitution mutation homologous to His63Ser in the RB49 UvsX amino acid sequence, a substitution mutation homologous to Pro321Lys in the RB49 UvsX amino acid sequence, a substitution mutation homologous to Asp334Lys in the RB49 UvsX amino acid sequence, and/or substitution mutations homologous to Pro321Lys and Asp334Lys in the RB49 UvsX amino acid sequence.

In some aspects, an altered recombinase includes any of the recombinant UvsX recombinases discussed above, further having a mutation selected from the addition of one or more glutamic acid residues at the C-terminus, the addition of one or more aspartic acid residues at the C-terminus, and a combination thereof.

The present invention includes an isolated nucleic acid molecule encoding an altered UvsX recombinase as described herein.

The present invention includes an expression vector including an isolated nucleic acid molecule encoding an altered UvsX recombinase as described herein.

The present invention includes a kit including one or more of the altered UvsX recombinases described herein, one or more of the isolated nucleic acid molecules encoding an altered UvsX recombinase as described herein, and/or one or more expression vectors including an isolated nucleic acid molecule encoding an altered UvsX recombinase as described herein.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1A is a schematic showing alignment of UvsX amino acid sequences from Enterobacteria phage T4 (T4) (SEQ ID NO: 8), Enterobacteria phage T6 (T6) (SEQ ID NO: 9), *Acinetobacter* phage 133 (Phage133) (SEQ ID NO: 10), Enterobacteria phage RB69 (Rb69) (SEQ ID NO: 11), *Aeromonas* phage Aeh1 (Aeh1) (SEQ ID NO: 12), *Aeromonas* phage 65 (Ae65) (SEQ ID NO: 13), *Vibrio* phage KVP40 (Kvp40) (SEQ ID NO: 14), Enterobacteria phage RB43 (Rb43) (SEQ ID NO: 15), *Prochlorococcus* phage P-SSM2 (PSSM2) (SEQ ID NO: 16), and *Prochlorococcus* phage P-SSM4 (PSSM4) (SEQ ID NO: 17), as also set forth in the incorporated materials of US 2009/0029421. Residues that are positionally and/or functionally equivalent to Pro321 and Asp334 in the RB49 UvsX amino acid sequence are boxed and indicated by a triangle symbol.

FIG. 1B is a schematic showing a continuation of the alignment set forth in FIG. 1A. Residues that are positionally and/or functionally equivalent to Pro321 and Asp334 in the RB49 UvsX amino acid sequence are boxed and indicated by a triangle symbol.

FIG. 2 is a schematic showing alignment of UvsX amino acid sequences from Enterobacteria phage RB49 (RB49) (SEQ ID NO: 1) and Enterobacteria phage T4 (T4) (SEQ ID NO: 8). Residues that are positionally and/or functionally equivalent to Pro256 in the RB49 UvsX amino acid sequence are highlighted. Residues that are positionally and/or functionally equivalent to Pro321 and Asp334 in the RB49 UvsX amino acid sequence are indicated by a triangle symbol.

DETAILED DESCRIPTION

Figure 3:
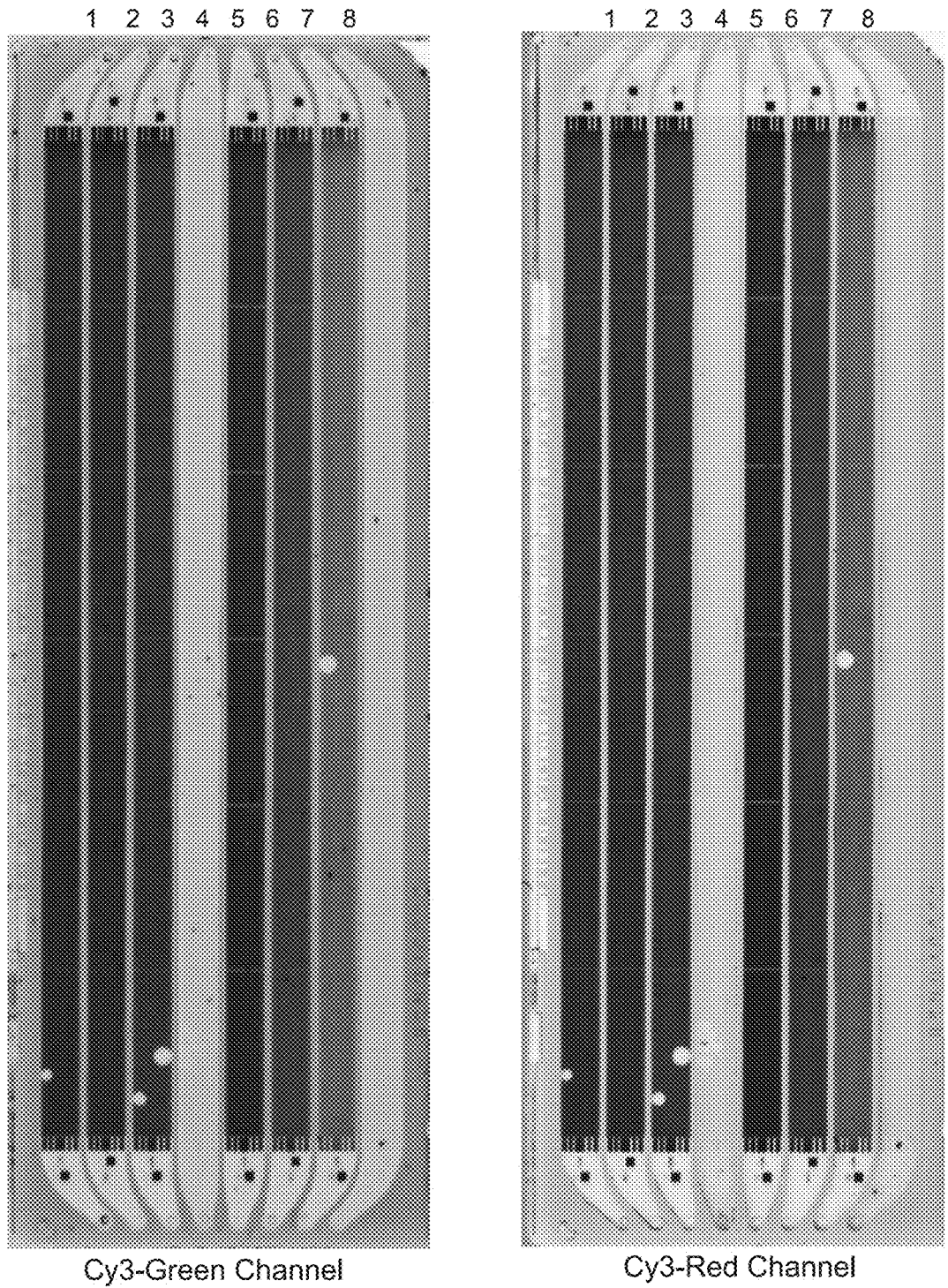
FIG. 3 is typhoon images of first cycle DNA sequencing imaged on a typhoon scanner measuring green fluorescence (G or T incorporation) and red fluorescence (A or C incorporation) of 150 pM Human PCR-free libraries clustered with V2 chemistry on 700 nM pitch v2.5 pFC. Lane 1 is H63S P256K. Lane 2 is H63S P321K D334K in buffer 1. Lane 3 is H63S P321K D334K in buffer 2. Lane 4 is Wt RB69 UvsX. Lane 5 is H63S P256K. Lane 6 is H63S P321K D334K in buffer 1. Lane 7 is H63S P321K D334K in buffer 2. Lane 8 is with no DNA. Buffer 1 is 20 mM Tris pH 7.5, 200 mM NaCl, 1 mM EDTA, and 1 mM BME. Buffer 2 is 50 mM Tris PH 7.5, 100 mM NaCL, 1 mM DTT, 0.1 mM EDTA, and 50% Glycerol.

Presented herein are recombinases for improved recombinase-mediated amplification of nucleic acids. The present inventors have surprisingly identified certain altered recombinases which have substantially improved characteristics in the seeding of nucleic acids onto a patterned flow cell surface.

As described in greater detail hereinbelow, the inventors have surprisingly found that one or more mutations to one or more residues in the recombinase result in profound improvements in seeding a DNA library, such as, for example, a PCR-library having single-stranded adapter regions, on a patterned flow cell surface, giving improved cluster amplification.

In certain embodiments, the substitution mutation comprises a mutation to a residue having a charged side chain. For example, in some embodiments, the charged amino acid is a positively charged amino acid residue. The term "positively charged amino acid" refers to a hydrophilic amino acid with a side chain pKa value of greater than 7, namely a basic amino acid. Basic amino acids typically have positively charged side chains at physiological pH due to association with a hydronium ion. Naturally occurring (genetically encoded) basic amino acids include lysine (Lys, K), arginine (Arg, R) and histidine (His, H), while non-natural (non-genetically encoded, or non-standard) basic amino acids include, for example, ornithine, 2,3,-diaminopropionic acid, 2,4-diaminobutyric acid, 2,5,6-triaminohexanoic acid, 2-amino-4-guanidinobutanoic acid, and homoarginine. The term "negatively charged amino acid" refers to a natural or non-natural amino acid, regardless of chirality, containing, in addition to the C-terminal carboxyl group, at least one additional negatively charged group such as carboxyl, phosphate, phosphonate, sulfonate, or the like.

Also presented herein is a recombinant UvsX recombinase comprising a substitution mutation to a semi-conserved domain of the recombinant UvsX. As used herein, the term "semi-conserved domain" refers to a portion of the recombinant UvsX that is fully conserved, or at least partially conserved among various species. It has been surprisingly discovered that mutation of one or more residues in the semi-conserved domain affects the recombinase activity especially in the presence of single-strand template nucleic acid, resulting in enhancement of seeding and/or amplification in recombinase-mediated amplification reactions. These mutated recombinases have improved performance in seeding of PCR-free libraries, such as a PCR-library having single-stranded adapter regions, on a patterned flow cell surface, resulting in improved cluster amplification, as described in the Example section below.

Figure 1A:
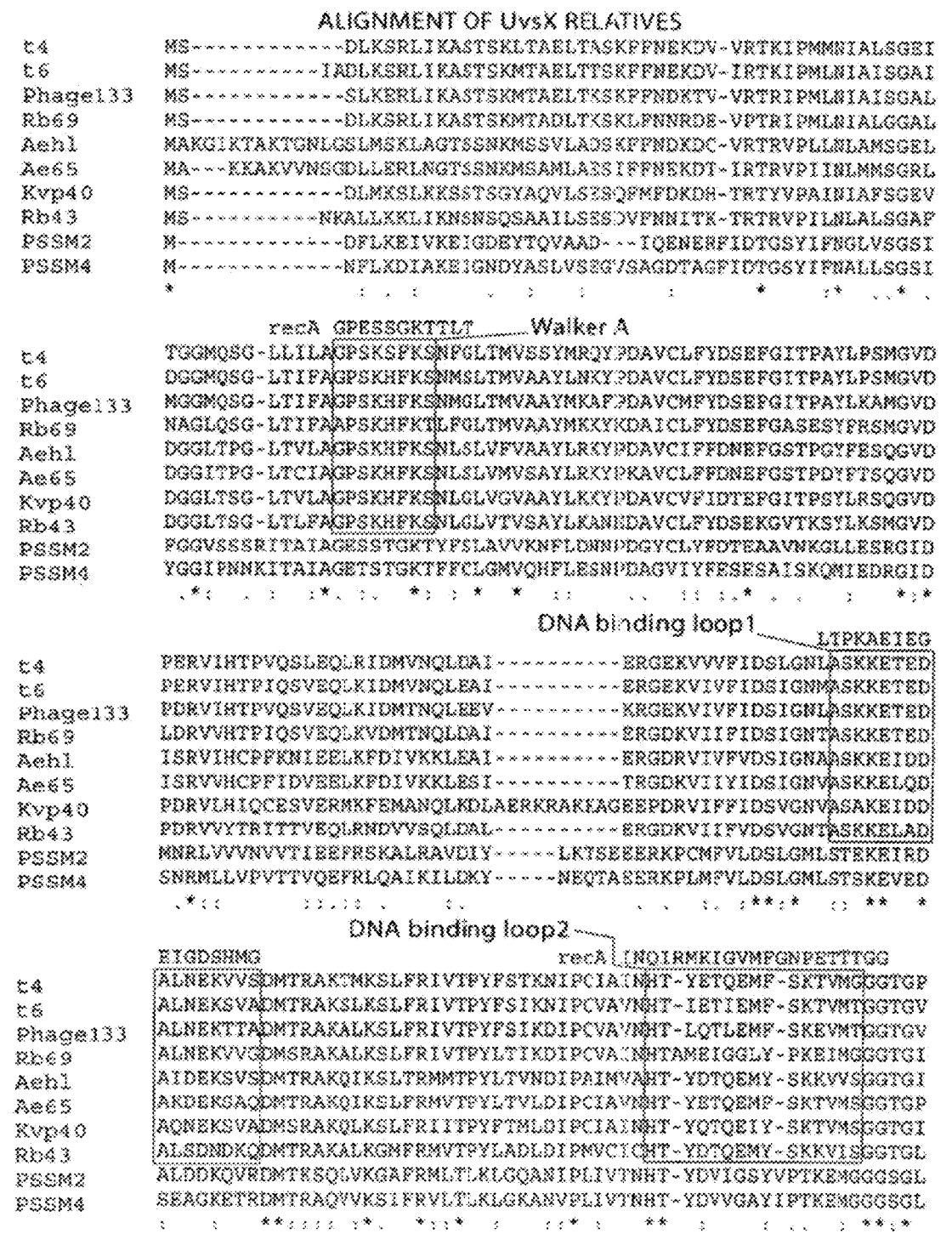

In some embodiments, the semi-conserved domain comprises amino acids having the sequence set forth in any of SEQ ID NOs: 3-4. SEQ ID NOs: 3-4 correspond to residues in the semi-conserved domain among various species. SEQ ID NO: 3 corresponds to residues 319-323 of the T4 UvsX amino acid sequence, which is set forth herein as SEQ ID NO: 8. An alignment showing the conservation among various species in the semi-conserved domain is set forth in FIGS. 1 and 2. The UvsX sequences shown in FIG. 1 were obtained from Genbank database accession numbers NP_049656 (T4), YP_004300647 (Phage 133); NP_861734 (RB69); NP_943894.1 (Aeh1); YP_004300858 (Ae65); NP_899256 (KVP40); YP_239013 (RB43); YP_214417 (P-SSM2); YP_214708 (P-SSM4); and from US Publication No. 2009/0029421 (T6). FIG. 2 is a schematic showing alignment of UvsX amino acid sequences from Enterobacteria phage RB49 (RB49) (SEQ ID NO: 1) and Enterobacteria phage T4 (T4) (SEQ ID NO: 8). Residues that are positionally and/or functionally equivalent to Pro256 in the RB49 UvsX amino acid sequence are highlighted. Residues that are positionally and/or functionally equivalent to Pro321 and Asp334 in the RB49 UvsX amino acid sequence are indicated by a triangle symbol. The UvsX sequences shown in FIG. 2 were obtained from Genbank database accession numbers NP_891595 (RB49) and NP_049656 (T4).

Mutations to one or more residues in the semi-conserved domain have been surprisingly found to increases the recombinase activity especially in the presence of single-strand template nucleic acid, resulting in enhancement of seeding and/or amplification in recombinase-mediated amplification reactions. These mutated recombinases have improved performance in seeding of PCR-free libraries, such as a PCR-library having single-stranded adapter regions, on a patterned flow cell surface, resulting in improved cluster amplification, as described in the Example section below. For example, in some embodiments of the recombinant UvsX presented herein, the substitution mutation comprises a mutation at position 4 of any of SEQ ID NOs: 3-4 to any residue other than other than Phe or Asp. In certain embodiments, the recombinant UvsX comprises a mutation to Lys at position 4 of any of SEQ ID NOs: 3-4.

In some embodiments, the semi-conserved domain comprises amino acids having the sequence set forth in any of SEQ ID NOs: 5-6. SEQ ID NOs: 5-6 correspond to residues in the semi-conserved domain among various species. SEQ ID NO: 5 corresponds to residues 332-337 of the T4 UvsX amino acid sequence, which is set forth herein as SEQ ID NO: 8. An alignment showing the conservation among various species in the semi-conserved domain is set forth in FIGS. 1 and 2.

In some embodiments of the recombinant UvsX presented herein, the substitution mutation comprises a mutation at position 4 of any of SEQ ID NOs: 5-6 to any residue other than Arg or Asp. In certain embodiments, the recombinant UvsX comprises a mutation to Lys at position 4 of any of SEQ ID NOs: 5-6.

In some embodiments, the semi-conserved domain comprises amino acids having the sequence set forth in any of SEQ ID NO: 36 or SEQ ID NO: 7. SEQ ID NO: 7 corresponds to residues in the semi-conserved domain among various species. SEQ ID NO: 36 corresponds to residues 329-337 of the T4 UvsX amino acid sequence, which is set forth herein as SEQ ID NO: 8. An alignment showing the conservation among various species in the semi-conserved domain is set forth in FIGS. 1 and 2.

In some embodiments of the recombinant UvsX presented herein, the substitution mutation comprises a mutation at position 7 of any of SEQ ID NO: 36 or SEQ ID NO: 7 to any residue other than Arg, Thr, Asn, Glu, or Asp. In certain embodiments, the recombinant UvsX comprises a mutation to Lys at position 7 of any of SEQ ID NO:36 or SEQ ID NO: 7.

In some embodiments, the recombinase is a UvsX protein. Any phage recombinase can be used in the embodiments presented herein, including, for example phage recombinases such as UvsX or UvsX-like recombinase derived from a myoviridae phage such as, for example, T4, T6, Rb69, Aeh1, KVP40, *Acinetobacter* phage 133, *Aeromonas* phage 65, cyanophage P-SSM2, cyanophage PSSM4, cyanophage S-PM2, Rb32, *Vibrio* phage nt-1, Rb16, Rb43, and Rb49. In certain embodiments, the recombinase is a UvsX or UvsX-like recombinase derived from a myoviridae phage such as, for example, T2, Rb14, *Aeromonas* phage 25, phi-1, Phage 31, phage 44RR2.8t, phage Rb3, and phage LZ2. It will be readily apparent to one of skill in the art that other recombinase proteins can be used in the embodiments presented herein. Suitable recombinase proteins can be identified by homology to UvsX using any number of a number of methods known in the art, such as, for example, BLAST alignment, as described in greater detail below.

By "functionally equivalent" it is meant that the control recombinase, in the case of studies using a different recombinase entirely, will contain the amino acid substitution that is considered to occur at the amino acid position in the other recombinase that has the same functional role in the enzyme. As an example, the mutation at position 322 from Proline to Lysine (P322K) in the T4 UvsX would be functionally equivalent to a substitution at position 321 from Proline to Lysine (P321K) in RB49 UvsX. Similarly, the mutation at position 335 from Arginine to Lysine (R335K) in the T4 UvsX would be functionally equivalent to a substitution at position 334 from Aspartate to Lysine (D334K) in RB49 UvsX.

Generally functionally equivalent substitution mutations in two or more different recombinases occur at homologous amino acid positions in the amino acid sequences of the recombinases. Hence, use herein of the term "functionally equivalent" also encompasses mutations that are "positionally equivalent" or "homologous" to a given mutation, regardless of whether or not the particular function of the mutated amino acid is known. It is possible to identify positionally equivalent or homologous amino acid residues in the amino acid sequences of two or more different recombinases on the basis of sequence alignment and/or molecular modelling. An example of sequence alignment to identify positionally equivalent and/or functionally equivalent residues is set forth in FIG. 1, which sets forth an alignment of UvsX amino acid sequences from Enterobacteria phage T4 (T4) (SEQ ID NO: 8), Enterobacteria phage T6 (T6) (SEQ ID NO: 9), *Acinetobacter* phage 133 (Phage133) (SEQ ID NO: 10), Enterobacteria phage RB69 (Rb69) (SEQ ID NO: 11), *Aeromonas* phage Aeh1 (Aeh1) (SEQ ID NO: 12), *Aeromonas* phage 65 (Ae65) (SEQ ID NO: 13), *Vibrio* phage KVP40 (Kvp40) (SEQ ID NO: 14), Enterobacteria phage RB43 (Rb43) (SEQ ID NO: 15), *Prochlorococcus* phage P-SSM2 (PSSM2) (SEQ ID NO: 16), and *Prochlorococcus* phage P-SSM4 (PSSM4) (SEQ ID NO: 17), as also set forth in the incorporated materials of US 2009/0029421. The UvsX sequences shown in FIG. 1 were obtained from Genbank database accession numbers NP_049656 (T4), YP_004300647 (Phage 133); NP_861734 (RB69); NP_943894.1 (Aeh1); YP_004300858 (Ae65); NP_899256 (KVP40); YP_239013 (RB43); YP_214417 (P-SSM2); YP_214708 (P-SSM4); and from US Publication No. 2009/0029421 (T6).

FIG. 2 is a schematic showing alignment of UvsX amino acid sequences from Enterobacteria phage RB49 (RB49) (SEQ ID NO: 1) and Enterobacteria phage T4 (T4) (SEQ ID NO: 8). Residues that are positionally and/or functionally equivalent to Pro256 in the RB49 UvsX amino acid sequence are highlighted. Residues that are positionally and/or functionally equivalent to Pro321 and Asp334 in the RB49 UvsX amino acid sequence are highlighted and indicated by a triangle. The UvsX sequences shown in FIG. 2 were obtained from Genbank database accession numbers NP_891595 (RB49) and NP_049656 (T4).

A positionally equivalent and/or functionally equivalent residue can be determined for one or more of any number of other UvsX sequences by aligning those sequences with that of a reference sequence such as T4 and RB49. As a non-limiting example, UvsX sequences from *Synechococcus* phage S-PM2, Enterobacteria phage RB32, *Vibrio* phage nt-1, Enterobacteria phage RB16 are set forth as SEQ ID NOs: 18-21, and obtained from Genbank database accession numbers YP_195169.1; YP_802982.1; YP_008125207.1; YP_003858336.1, can be aligned with a reference UvsX sequence such as, for example T4 UvsX (SEQ ID NO: 8) and RB49 UvsX (SEQ ID NO: 1) and positionally equivalent and/or functionally equivalent residues are identified. By way of example, the residues shown in Table 1 below are identified as positionally equivalent and/or functionally equivalent to Pro321 and Asp334 in the RB49 UvsX amino acid sequence. It will be readily appreciated by one of skill in the art that positionally equivalent and/or functionally equivalent positions for other UvsX proteins can be ascertained by following a similar approach.

TABLE 1

| Phage Species | SEQ ID NO: | Positionally/ Functionally Equivalent Position to RB49 Pro321 | Positionally/ Functionally Equivalent Position to RB49 Asp334 |
|---|---|---|---|
| T4 | 8 | Pro322 | Arg335 |
| T6 | 9 | Pro 324 | Arg337 |
| Acinetobacter phage 133 | 10 | Pro320 | Thr333 |
| Rb69 | 11 | Pro323 | Thr336 |
| Aeh1 | 12 | Pro334 | Asp347 |
| Aeromonas phage 65 | 13 | Pro333 | Asn346 |
| KVP40 | 14 | Asp332 | Arg345 |
| Rb43 | 15 | Pro324 | Asp337 |
| cyanophage P-SSM2 | 16 | | Glu328 |
| cyanophage PSSM4 | 17 | | Lys330 |
| cyanophage S-PM2 | 18 | | Arg331 |
| Rb32 | 19 | Pro324 | Arg337 |
| Vibrio phage nt-1 | 20 | Glu332 | Arg345 |
| Rb16 | 21 | Pro324 | Asp337 |

The recombinant UvsX proteins described hereinabove can comprise additional substitution mutations that are known to enhance one or more aspects of recombinase activity, stability or any other desirable property. For example, in some embodiments, in addition to any of the above mutations, the recombinant UvsX can further comprise substitution mutations at positions functionally equivalent His63 in the RB49 UvsX amino acid sequence as is known in the art and exemplified by the disclosure of US 2009/0029421, which is incorporated by reference in its entirety. For example, in certain embodiments, the recombinant UvsX comprises a substitution mutation homologous to His63Ser in the RB49 UvsX amino acid sequence.

In some embodiments, in addition to any of the above mutations, the recombinant UvsX can further comprise substitution mutations at positions functionally equivalent Pro256 in the RB49 UvsX amino acid sequence as is known in the art and exemplified by the disclosure of U.S. application Ser. No. 14/869,744, filed on Sep. 29, 2015, and entitled "Recombinase Mutants," which is incorporated by reference in its entirety. For example, in certain embodiments, the recombinant UvsX comprises a substitution mutation homologous to Pro256Lys in the RB49 UvsX amino acid sequence.

In some embodiments, an altered recombinase includes an Enterobacteria phage RB49 UvsX having the amino acid sequence SEQ ID NO: 1 with an alteration at Pro321, Asp334, and/or Pro256, including, for example, the alteration P321K, the alteration D334K, the alterations P321K and D334K, and the alterations P321K, D334K, and P256K. Such an altered recombinase may further include the alteration H63S, including for example, the alterations H63S and P321K, the alterations H63S and D334K, the alterations H63S, P321K, and D334K, the alterations H63S and P256K, and the alterations H63S, P321K, D334K, and P256K.

In some embodiments, an altered recombinase includes an Enterobacteria phage T4 UvsX having the amino acid sequence SEQ ID NO: 8 with an alteration at Pro322, Arg335, and/or Phe 257, including, for example, the alteration P322K, the alteration R335K, the alterations P322K and R335K, and the alterations F257K, P322K and R335K.

In some embodiments, an altered recombinase includes an Enterobacteria phage T6 UvsX having the amino acid sequence SEQ ID NO: 9 with an alteration at Pro324, Arg337, and/or Phe259, including, for example, the alteration P324K, the alteration R337K, the alterations P324K and R337K, and the alterations F259K, P324K, and R337K. Such an altered recombinase may further include the alteration H66S, including for example, the alterations H66S and P324K, the alterations H66S and R337K, the alterations H66S, P324K, and R337K, and the alterations H66S, F259K, P324K and R337K.

In some embodiments, an altered recombinase includes an Acinetobacter phage 133 UvsX having the amino acid sequence SEQ ID NO: 10 with an alteration at Pro320, Thr333, and/or Pro257, including, for example, the alteration P320K, the alteration T333K, the alterations P320K and T333K, and the alterations P257K, P320K, and T333K. Such an altered recombinase may further include the alteration H64S, including, for example, the alterations H64S and P320K, the alterations H64S and T333K, the alterations H64S, P320K, and T333K, and the alterations H64S, P257K, P320K, and T333K.

In some embodiments, an altered recombinase includes an Enterobacteria phage RB69 UvsX having the amino acid sequence SEQ ID NO: 11 with an alteration at Pro258, Pro323, and/or Thr336, including, for example, the alteration P323K, the alteration T336K, the alterations P323K and T336K, and the alterations P258K, P323K, and T336K. Such an altered recombinase may further include the alteration H64S, including, for example, the alterations H64S and P323K, the alterations H64S and T336K, the alterations H64S, P323K, and T336K, and the alterations H64S, P258K, P323K, and T336K.

In some embodiments, an altered recombinase includes a UvsX recombinase derived from the Aeromonas phage Aeh1 UvsX having the amino acid sequence SEQ ID NO: 12 with an alteration at Pro269, Pro334, and/or Asp347, including, for example, the alteration P334K, the alteration D347K, the alterations P334K and D347K, and the alterations P269K, P334K, and D347K. Such an altered recombinase may further include the alteration H76S, including, for example, the alterations H76S and P334K, the alterations H76S and D347K, the alterations H76S, P334K, and D347K, and the alterations H76S, P269K, P334K, and D347K.

In some embodiments, an altered recombinase includes a UvsX recombinase derived from the Aeromonas phage 65 UvsX having the amino acid sequence SEQ ID NO: 13 with an alteration at Asp226, Pro333, and/or Asn346, including, for example, the alteration P333K, the alteration N346K, the alterations P333K and N236K, and the alterations D266K, P333K, and N236K. Such an altered recombinase may further include the alteration H73S, including, for example, the alterations H73S and P333K, the alterations H73S and N346K, the alterations H73S, P333K, and N236K, and the alterations H73S, D266K, P333K, and N236K.

In some embodiments, an altered recombinase includes a UvsX recombinase derived from the Vibrio phage KVP40 UvsX having the amino acid sequence SEQ ID NO: 14 with an alteration at Pro267, Asp332, and/or Arg345, including, for example, the alteration D332K, the alteration R345K, the alterations D332K and R345K, and the alterations P267K, D332K and R345K. Such an altered recombinase may further include the alteration H64S, including, for example, the alterations H64S and D332K, the alterations H64S and R345K, the alterations H64S, D332K, and R345K, and the alterations H64S, P267K, D332K, and R345K.

In some embodiments, an altered recombinase includes an Enterobacteria phage RB43 UvsX having the amino acid sequence SEQ ID NO: 15 with an alteration at Pro259, Pro324, and/or Asp337, including, for example, the alteration P324K, the alteration D337K, the alterations P324K and D337K, and the alterations P259K, P324K, and D337K. Such an altered recombinase may further include the alteration H66S, including, for example, the alterations H66S and P324K, the alterations H66S and D337K, the alterations H66Sm P324K, and D337K, and the alterations H66S, P259K, P324K, and D337K.

In some embodiments, an altered recombinase includes a UvsX recombinase derived from the *Prochlorococcus* phage P-SSM2 UvsX having the amino acid sequence SEQ ID NO: 16 with an alteration at Gln261 and/or Glu328, including, for example, the alteration E328K and the alterations Q261K and E328K. Such an altered recombinase may further include the alteration T62S, including, for example, the alteration T62S and E328K and the alterations T62S, Q261K, and E328K.

In some embodiments, an altered recombinase includes a *Prochlorococcus* phage P-SSM4 UvsX having the amino acid sequence SEQ ID NO: 17 with an alteration at Lys330, including, for example, an alteration at K330. Such an altered recombinase may further include the alteration T65S.

In some embodiments, an altered recombinase includes a *Synechococcus* phage S-PM2 UvsX having the amino acid sequence SEQ ID NO: 18 with an alteration at Arg331 and/or Glu264, including, for example, the alteration R331K and the alteration E264K and R331K. Such an altered recombinase may further include the alteration T65S, including, for example, the alterations T65S and R331K and the alteration T65S, E264K, and R331K.

In some embodiments, an altered recombinase includes an Enterobacteria phage RB32 UvsX having the amino acid sequence SEQ ID NO: 19 with an alteration at Pro324 and/or Arg337, including, for example, the alteration P324K, the alteration R337K, and the alterations P324K and R337K. Such an altered recombinase may further include the alteration H66S, including, for example, the alterations H66S and P324K, the alterations H66S and R337K, and the alterations H66S, P324K, and R337K.

In some embodiments, an altered recombinase includes a *Vibrio* phage nt-1 UvsX having the amino acid sequence SEQ ID NO: 20 with an alteration at Phe259, Glu332, and/or Arg345, including, for example, the alteration E332K, the alteration R345K, the alterations E332K and R345K, and the alterations F259, E332K, and R345K. Such an altered recombinase may further include the alteration H64S, including, for example, the alterations H64S and E332K, the alterations H64S and R345K, the alterations H64S, E332K, and R345K, and the alterations H64S, F259, E332K, and R345K.

In some embodiments, an altered recombinase includes an Enterobacteria phage RB16 UvsX having the amino acid sequence SEQ ID NO: 21 with an alteration at Pro259, Pro324, and/or Asp337, including, for example, the alteration P324K, the alteration D337K, the alterations P324K and D337K, and the alterations P259K, P324K, and D337K. Such an altered recombinase may further include the altera-tion H66S, including, for example, the alterations H66S and P324K, the alterations H66S and D337K, the alterations H66S, P324K, and D337K, and the alterations H66S, P259K, P324K, and D337K.

In some embodiments, an altered recombinase includes an UvsX recombinase as described in any one of Tables 1 to 5 included herewith.

In some embodiments, in addition to any of the above mutations, the recombinant UvsX can comprise additional substitution, deletion and/or addition mutations as compared to a wild type recombinase. Any of a variety of substitution mutations at one or more of positions can be made, as is known in the art and exemplified by the materials of 2009/0029421, which is incorporated by reference in its entirety. For example, in some embodiments, in addition to the above mutations, the recombinant UvsX can further comprise a mutation selected from the group consisting of: the addition of one or more glutamic acid residues at the C-terminus; the addition of one or more aspartic acid residues at the C-terminus; and a combination thereof.

Mutating Recombinases

Various types of mutagenesis are optionally used in the present disclosure, for example, to modify recombinases to produce variants, for example, in accordance with recombinase models and model predictions, or using random or semi-random mutational approaches. In general, any available mutagenesis procedure can be used for making recombinase mutants. Such mutagenesis procedures optionally include selection of mutant nucleic acids and polypeptides for one or more activity of interest (for example, enhanced seeding and/or amplification on a solid support). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting recombinase for mutation can be any of those noted herein, including available recombinases mutants such as those identified for example, in US 2009/0029421, which is incorporated by reference in its entirety.

Optionally, mutagenesis can be guided by known information from a naturally occurring recombinase molecule, or of a known altered or mutated recombinase (for example, using an existing mutant recombinase as noted in the preceding references), for example, sequence, sequence comparisons, physical properties, crystal structure and/or the like as discussed above. However, in another class of embodiments, modification can be essentially random (for example, as in classical or "family" DNA shuffling, see, for example, Crameri et al. (1998) "DNA shuffling of a family of genes from diverse species accelerates directed evolution" *Nature* 391:288-291).

Additional information on mutation formats is found in: Sambrook et al., Molecular Cloning—A Laboratory Manual (3rd Ed.), Vol. 1-3, Cold Spring Harbor Laboratory, Cold Spring Harbor, N.Y., 2000 ("Sambrook"); Current Protocols in Molecular Biology, F. M. Ausubel et al., eds., Current Protocols, a joint venture between Greene Publishing Associates, Inc. and John Wiley & Sons, Inc., (supplemented through 2011) ("Ausubel")) and PCR Protocols A Guide to Methods and Applications (Innis et al. eds) Academic Press Inc. San Diego, Calif. (1990) ("Innis"). The following publications and references cited within provide additional detail on mutation formats: Arnold, "Protein engineering for unusual environments," *Current Opinion in Biotechnology* 4:450-455 (1993); Bass et al., "Mutant Trp repressors with new DNA-binding specificities," *Science* 242:240-245 (1988); Bordo and Argos (1991) "Suggestions for "Safe" Residue Substitutions" in *Site-directed Mutagenesis* 217: 721-729; Botstein and Shortie, "Strategies and applications of in vitro mutagenesis," *Science* 229:1193-1201 (1985); Carter et al., "Improved oligonucleotide site-directed mutagenesis using M13 vectors," *Nucl Acids Res* 13: 4431-4443 (1985); Carter, "Site-directed mutagenesis," *Biochem J* 237: 1-7 (1986); Carter, "Improved oligonucleotide-directed mutagenesis using M13 vectors," *Methods in Enzymol* 154: 382-403 (1987); Dale et al., "Oligonucleotide-directed random mutagenesis using the phosphorothioate method," *Methods Mol. Biol.* 57:369-374 (1996); Eghtedarzadeh and Henikoff, "Use of oligonucleotides to generate large deletions," *Nucl. Acids Res.* 14: 5115 (1986); Fritz et al., "Oligonucleotide-directed construction of mutations: a gapped duplex DNA procedure without enzymatic reactions in vitro," *Nucl. Acids Res.* 16: 6987-6999 (1988); Grundstrom et al., "Oligonucleotide-directed mutagenesis by microscale 'shot-gun' gene synthesis," *Nucl. Acids Res.* 13: 3305-3316 (1985); Hayes (2002) "Combining Computational and Experimental Screening for rapid Optimization of Protein Properties," *PNAS* 99(25) 15926-15931; Kunkel, "The efficiency of oligonucleotide directed mutagenesis," in Nucleic Acids & Molecular Biology (Eckstein, F. and Lilley, D. M. J. eds., Springer Verlag, Berlin)) (1987); Kunkel, "Rapid and efficient site-specific mutagenesis without phenotypic selection," *PNAS* 82:488-492 (1985); Kunkel et al., "Rapid and efficient site-specific mutagenesis without phenotypic selection," *Methods in Enzymol.* 154, 367-382 (1987); Kramer et al., "The gapped duplex DNA approach to oligonucleotide-directed mutation construction," *Nucl. Acids Res.* 12: 9441-9456 (1984); Kramer and Fritz, "Oligonucleotide-directed construction of mutations via gapped duplex DNA," *Methods in Enzymol.* 154:350-367 (1987); Kramer et al., "Point Mismatch Repair," *Cell* 38:879-887 (1984); Kramer et al., "Improved enzymatic in vitro reactions in the gapped duplex DNA approach to oligonucleotide-directed construction of mutations," *Nucl. Acids Res.* 16: 7207 (1988); Ling et al., "Approaches to DNA mutagenesis: an overview," *Anal Biochem.* 254(2): 157-178 (1997); Lorimer and Pastan, *Nucleic Acids Res.* 23, 3067-8 (1995); Mandecki, "Oligonucleotide-directed double-strand break repair in plasmids of *Escherichia coli*: a method for site-specific mutagenesis," *Proc. Natl. Acad. Sci. USA,* 83:7177-7181 (1986); Nakamaye and Eckstein, "Inhibition of restriction endonuclease NciI cleavage by phosphorothioate groups and its application to oligonucleotide-directed mutagenesis," *Nucl. Acids Res.* 14: 9679-9698 (1986); Nambiar et al., "Total synthesis and cloning of a gene coding for the ribonuclease S protein," *Science* 223: 1299-1301 (1984); Sakamar and Khorana, "Total synthesis and expression of a gene for the a-subunit of bovine rod outer segment guanine nucleotide-binding protein (transducin)," *Nucl. Acids Res.* 14: 6361-6372 (1988); Sayers et al., "Y-T Exonucleases in phosphorothioate-based oligonucleotide-directed mutagenesis," *Nucl. Acids Res.* 16:791-802 (1988); Sayers et al., "Strand specific cleavage of phosphorothioate-containing DNA by reaction with restriction endonucleases in the presence of ethidium bromide," *Nucl. Acids Res.* 16: 803-814 (1988); Sieber, et al., *Nature Biotechnology* 19:456-460 (2001); Smith, "In vitro mutagenesis," *Ann. Rev. Genet.* 19:423-462 (1985); *Methods in Enzymol.* 100: 468-500 (1983); *Methods in Enzymol.* 154: 329-350 (1987); Stemmer, *Nature* 370, 389-91 (1994); Taylor et al., "The use of phosphorothioate-modified DNA in restriction enzyme reactions to prepare nicked DNA," *Nucl. Acids Res.* 13: 8749-8764 (1985); Taylor et al., "The rapid generation of oligonucleotide-directed mutations at high frequency using phosphorothioate-modified DNA," *Nucl. Acids Res.* 13: 8765-8787 (1985); Wells et al., "Importance of hydrogen-bond formation in stabilizing the transition state of subtilisin," *Phil. Trans. R. Soc. Lond. A* 317: 415-423 (1986); Wells et al., "Cassette mutagenesis: an efficient method for generation of multiple mutations at defined sites," *Gene* 34:315-323 (1985); Zoller and Smith, "Oligonucleotide-directed mutagenesis using M 13-derived vectors: an efficient and general procedure for the production of point mutations in any DNA fragment," *Nucleic Acids Res.* 10:6487-6500 (1982); Zoller and Smith, "Oligonucleotide-directed mutagenesis of DNA fragments cloned into M13 vectors," *Methods in Enzymol.* 100:468-500 (1983); Zoller and Smith, "Oligonucleotide-directed mutagenesis: a simple method using two oligonucleotide primers and a single-stranded DNA template," *Methods in Enzymol.* 154:329-350 (1987); Clackson et al., "Making antibody fragments using phage display libraries," *Nature* 352:624-628 (1991); Gibbs et al., "Degenerate oligonucleotide gene shuffling (DOGS): a method for enhancing the frequency of recombination with family shuffling," *Gene* 271:13-20 (2001); and Hiraga and Arnold, "General method for sequence-independent site-directed chimeragenesis," *J. Mol. Biol.* 330:287-296 (2003). Additional details on many of the above methods can be found in *Methods in Enzymology* Volume 154, which also describes useful controls for trouble-shooting problems with various mutagenesis methods.

Making and Isolating Recombinant Recombinase

Generally, nucleic acids encoding a recombinase as presented herein can be made by cloning, recombination, in vitro synthesis, in vitro amplification and/or other available methods. A variety of recombinant methods can be used for expressing an expression vector that encodes a recombinase as presented herein. Methods for making recombinant nucleic acids, expression and isolation of expressed products are well known and described in the art. A number of exemplary mutations and combinations of mutations, as well as strategies for design of desirable mutations, are described herein.

Additional useful references for mutation, recombinant and in vitro nucleic acid manipulation methods (including cloning, expression, PCR, and the like) include Berger and Kimmel, Guide to Molecular Cloning Techniques, *Methods in Enzymology* Volume 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and The Nucleic Acid Protocols Handbook Ralph Rapley (ed) (2000) Cold Spring Harbor, Humana Press Inc (Rapley); Chen et al. (ed) PCR Cloning Protocols, Second Edition (Methods in Molecular Biology, volume 192) Humana Press; and in Viljoen et al. (2005) Molecular Diagnostic PCR Handbook Springer, ISBN 1402034032.

In addition, a plethora of kits are commercially available for the purification of plasmids or other relevant nucleic acids from cells, (see, for example, EASY PREP™ and FLEXIPRPEP™, both from Pharmacia Biotech; STRATA-CLEAN™, from Stratagene; and QIAPREP™, from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (for example, shuttle vectors) and selection markers for both prokaryotic and eukaryotic systems. Vectors are suitable for replication and integration in prokaryotes, eukaryotes, or both.

Other useful references, for example, for cell isolation and culture (for example, for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, Fla.

Nucleic acids encoding the recombinant recombinases of disclosed herein are also a feature of embodiments presented herein. A particular amino acid can be encoded by multiple codons, and certain translation systems (for example, prokaryotic or eukaryotic cells) often exhibit codon bias, for example, different organisms often prefer one of the several synonymous codons that encode the same amino acid. As such, nucleic acids presented herein are optionally "codon optimized," meaning that the nucleic acids are synthesized to include codons that are preferred by the particular translation system being employed to express the recombinase. For example, when it is desirable to express the recombinase in a bacterial cell (or even a particular strain of bacteria), the nucleic acid can be synthesized to include codons most frequently found in the genome of that bacterial cell, for efficient expression of the recombinase. A similar strategy can be employed when it is desirable to express the recombinase in a eukaryotic cell, for example, the nucleic acid can include codons preferred by that eukaryotic cell.

A variety of protein isolation and detection methods are known and can be used to isolate recombinases, for example, from recombinant cultures of cells expressing the recombinant recombinases presented herein. A variety of protein isolation and detection methods are well known in the art, including, for example, those set forth in R. Scopes, Protein Purification, Springer-Verlag, N.Y. (1982); Deutscher, *Methods in Enzymology* Vol. 182: Guide to Protein Purification, Academic Press, Inc. N.Y. (1990); Sandana (1997) Bioseparation of Proteins, Academic Press, Inc.; Bollag et al. (1996) Protein Methods, 2nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein. Additional details regarding protein purification and detection methods can be found in Satinder Ahuj a ed., Handbook of Bioseparations, Academic Press (2000).

Methods of Use

The altered recombinases presented herein can be used in a recombinase-mediated amplification procedure, such as a recombinase polymerase amplification (RPA) technique. Briefly, RPA can be initiated by contacting a target nucleic acid with a recombinase and a single stranded nucleic acid primer specific for the target nucleic acid molecule. The hybridized primer can then be extended by a polymerase, such as a polymerase capable of strand displacement in the presence of dNTPs to generate a double stranded target nucleic acid molecule and a displaced strand of nucleic acid molecule. Further amplification can take place by recombinase-mediated targeting of primers to the displaced strand of nucleic acid molecule and extension of the primer to generate a double stranded nucleic acid molecule. The RPA process can be modulated by combination of the above-described components with, for example, recombinase-loading factors, specific strand-displacing polymerases and a robust energy regeneration system. Exemplary RPA procedures, systems and components that can be readily adapted for use with the recombinant UvsX proteins of the present disclosure are described, for example, in U.S. Pat. Nos. 8,071,308; 7,399,590; 7,485,428; 7,270,981; 8,030,000; 7,666,598; 7,763,427; 8,017,399; 8,062,850; and 7,435,561, each of which is incorporated herein by reference.

In some embodiments, isothermal amplification can be performed using kinetic exclusion amplification (KEA), also referred to as exclusion amplification (ExAmp). A nucleic acid library of the present disclosure can be made using a method that exploits kinetic exclusion. Kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of U.S. Application Pub. No. 2013/0338042, which is incorporated herein by reference in its entirety.

In some embodiments, the target nucleic acid that is amplified is fully double stranded. In some embodiments, the target nucleic acid that is amplified comprises a region of double stranded nucleic acid, and also comprises a region having single stranded nucleic acid. In certain embodiments, the target nucleic acid comprises one or more forked adapters with a region of about 5, 10, 15, 20, 25, 30, 35, 40 or more than about 40 bases of single stranded sequence at each end of the library fragments. Design and use of forked adapters is described in greater detail in the disclosures of U.S. Pat. Nos. 7,742,463 and 8,563,748, each of which is incorporated herein by reference in its entirety.

Kinetic exclusion can exploit a relatively slow rate for making a first copy of a target nucleic acid vs. a relatively rapid rate for making subsequent copies of the target nucleic acid or of the first copy. In the example of the previous paragraph, kinetic exclusion occurs due to the relatively slow rate of target nucleic acid seeding (for example, relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (for example, delayed or slow activation) vs. the relatively rapid rate at which subsequent copies are made to fill the site. In this example, an individual site may have been seeded with several different target nucleic acids (for example, several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and in some cases increase the rate of amplicon formation. Recombinase, such as for example UvsX, can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (for example via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (for example, DNAs encoding a recombinase, or the amino acid sequence of a recombinase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, for example, 30%, 40%, 50%, 60%, 70%, 80%, 90%, 95%, or 99% or more, can also be used to establish homology. Methods for determining sequence similarity percentages (for example, BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, *Proc. Natl. Acad. Sci. USA* 89:10915 (1989)).

In addition to calculating percent sequence identity, the BLAST algorithm also performs a statistical analysis of the similarity between two sequences (see, for example, Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Nucleic Acids Encoding Altered Recombinases

Further presented herein are nucleic acid molecules encoding the altered recombinase enzymes presented herein. For any given altered recombinase which is a mutant version of a recombinase for which the amino acid sequence and preferably also the wild type nucleotide sequence encoding the recombinase is known, it is possible to obtain a nucleotide sequence encoding the mutant according to the basic principles of molecular biology. For example, given that the wild type nucleotide sequence encoding RB49 UvsX recombinase is known, it is possible to deduce a nucleotide sequence encoding any given mutant version of RB49 UvsX having one or more amino acid substitutions using the standard genetic code. Similarly, nucleotide sequences can readily be derived for mutant versions other recombinases such as, for example, T4, T6, Rb69, Aeh1, KVP40, *Acinetobacter* phage 133, *Aeromonas* phage 65, cyanophage P-SSM2, cyanophage PSSM4, cyanophage S-PM2, Rb32, *Vibrio* phage nt-1, Rb16, Rb43, T2, Rb14, *Aeromonas* phage 25, phi-1, Phage 31, phage 44RR2.8t, phage Rb3, and phage LZ2, etc. Nucleic acid molecules having the required nucleotide sequence may then be constructed using standard molecular biology techniques known in the art.

In accordance with the embodiments presented herein, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the recombinase proteins encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular cloning: A Laboratory Manual, Cold Spring Harbor Laboratory, which is incorporated by reference in its entirety.

Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the embodiments presented herein.

The nucleic acid molecule may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the recombinase by higher eukaryotes may be optimised by including an enhancer sequence in the vector. Enhancers are cis-acting elements of DNA that act on a promoter to increase the level of transcription. Vectors will also generally include origins of replication in addition to the selectable markers.

Example 1

Evaluation of Mutants Having Mutations Homologous to P321K

The performance of recombinase mutants having mutations homologous to P321K is evaluated. In this example, "control" recombinases are generated by modifying the wild type recombinase to comprise a mutation homologous to the H63S in RB49, as set forth in the "control" column in the table below. The "P321K homolog" mutants are generated by further modifying the controls to bear a mutation homologous to the P321K in RB49 as set forth in the "P321K homolog" column in Table 2 below.

For example, for T6 UvsX, the control is generated by modifying wild type T6 UvsX (SEQ ID NO: 9) to bear a H66S mutation. The P321K homolog is further modified to bear both H66S and P324K mutations.

TABLE 2

| WT backbone | WT backbone SEQ ID NO: | Control | P321K homolog |
|---|---|---|---|
| RB49 | 1 | H63S | H63S P321K |
| T4 | 8 | 64S | 64S P322K |
| T6 | 9 | H66S | H66S P324K |
| Acinetobacter phage 133 | 10 | H64S | H64S P320K |
| Rb69 | 11 | H64S | H64S P323K |
| Aeh1 | 12 | H76S | H76S P334K |
| Aeromonas phage 65 | 13 | H73S | H73S P333K |
| KVP40 | 14 | H64S | H64S D332K |
| Rb43 | 15 | H66S | H66S P324K |
| Rb32 | 19 | H66S | P324K |
| Vibrio phage nt-1 | 20 | H64S | H64S E332K |
| Rb16 | 21 | H66S | H66S P324K |

Clustering of a PCR-free library on a patterned flow cell is performed on a cBot as described below, using either control or P321K mutant. Sequencing is then performed on a HiSeq instrument (Illumina, Inc.) and the sequencing results are analyzed as described below to determine callability of a variety of regions which are typically poorly represented in previous sequencing data.

A comparison of callability data for control vs. P321K homolog mutants demonstrates that the P321K homolog mutants show unexpected and significant improvements in callability of one or more of fosmid promoter regions, High GC, Huge GC, Low GC, High AT, Huge AT, and AT dinucleotide repeat regions, compared to that of the control.

Determination of Clustering Efficacy

In order to evaluate the efficacy of the mutant recombinase formulations in seeding a PCR-free library onto a patterned flow cell surface, a PCR-free library is generated using a TruSeq® DNA PCR-free sample preparation kit (Illumina, Inc.). PCR-free libraries generated using the TruSeq® library preparation kit have forked adapters with a region of about 40 bases of single stranded sequence at each end of the library fragments.

The library is mixed with the T4 UvsX formulation or the mutant recombinase formulation to 100 pM final concentration, flushed onto a flow cell, and incubated on a cBot at 38° C. After a 1 hour incubation period, the temperature is lowered to 20° C. and the flow cell is washed with HT2 wash buffer (Illumina). Clusters are stained with a 1:5,000 dilution of SYBR® Green (Life Technologies) in 0.1 M Tris/0.1 M sodium ascorbate and imaged on a fluorescence microscope. Based on the intensity of the fluorescence, it is determined that the density of clusters generated by seeding a PCR-free library onto a patterned flow cell using a formulation that includes the mutant recombinases is substantially improved.

Sequencing is then performed on a HiSeq instrument (Illumina, Inc.) and the sequencing results are analyzed to determine callability of a variety of regions which are typically poorly represented in previous sequencing data.

Callability is a measure of the fraction of sites at which a single nucleotide polymorphism (SNP) is called correctly. Ideally, this value is 1 (for 100%) meaning that at 100% of the sites within a particular type of region (i.e., high GC, etc) the SNPs are called correctly. Coverage is a measure of the fraction of sites which have a coverage >n, where n is typically 30× (i.e., the standard coverage for a human genome). The fosmid promoters are a set of 100 gene promoters which were identified as poorly represented in previous sequencing data. The promoters are cloned into fosmid vectors. A High GC region may be defined as a region with at least 100 bp where GC content is equal to or over 75% (N50 (G+C≥0.75) 100 N50). A Huge GC region may be defined as a region with at least 100 bp where GC content is equal to or over 85% (N50 (G+C≥0.85) 100 N50). A Low GC region may be defined as a region with at least 100 bp where GC content is equal to or less than 40% (N50 (G+C≥0.40) 100 N50). A High AT region may be defined as a region with at least 100 bp where AT content is equal to or over 75% (N50 (A+T≥0.75) 100 N50), downsampled to ~50 k regions. A Huge AT region may be defined as a region with at least 100 bp where AT content is equal to or over 85% (N50 (A+T≥0.85) 100 N50), downsampled to ~50K regions. An AT dinucleotide repeat region may be defined as a region that includes long stretches of ATAT repeats.

A comparison of callability data for control versus mutants demonstrates that the mutant shows unexpected and significant improvements in callability of one or more of fosmid promoter regions, High GC, Huge GC, Low GC, High AT, Huge AT, and AT dinucleotide repeat regions, compared to that of the control.

Example 2

Evaluation of Mutants Having Mutations Homologous to D334K

The performance of recombinase mutants having mutations homologous to D334K is evaluated. In this example, "control" recombinases are generated by modifying the wild type recombinase to comprise a mutation homologous to the H63S in RB49, as set forth in the "control" column in Table 3 below. The "D334K homolog" mutants are generated by further modifying the controls to bear a mutation homologous to the D334K in RB49 as set forth in the "D334K homolog" column in the table below.

For example, for T6 UvsX, the control is generated by modifying wild type T6 UvsX (SEQ ID NO: 9) to bear a H66S mutation. The D334K homolog is further modified to bear both H66S and R337K mutations.

TABLE 3

| WT backbone | WT backbone SEQ ID NO: | Control | D334K homolog |
|---|---|---|---|
| RB49 | 1 | H63S | H63S D334K |
| T4 | 8 | 64S | 64S R335 |
| T6 | 9 | H66S | H66S R337 |
| Acinetobacter phage 133 | 10 | H64S | H64S T333 |
| Rb69 | 11 | H64S | H64S T336 |
| Aeh1 | 12 | H76S | H76S D347 |
| Aeromonas phage 65 | 13 | H73S | H73S N346 |
| KVP40 | 14 | H64S | H64S R345 |
| Rb43 | 15 | H66S | H66S D337 |
| cyanophage P-SSM2 | 16 | T62S | T62S E328 |
| cyanophage PSSM4 | 17 | T65S | T65S K330 |
| cyanophage S-PM2 | 18 | T65S | T65S R331 |
| Rb32 | 19 | H66S | H66S R337 |
| Vibrio phage nt-1 | 20 | H64S | H64S R345 |
| Rb16 | 21 | H66S | H66S D337 |

Clustering of a PCR-free library on a patterned flow cell is performed on a cBot as described in Example 1 above, using either control or D334K mutant. Sequencing is then performed on a HiSeq instrument (Illumina, Inc.) and the sequencing results are analyzed as described in Example 1 above to determine callability of a variety of regions which are typically poorly represented in previous sequencing data.

A comparison of callability data for control vs. D334K homolog mutants demonstrates that the D334K homolog mutants show unexpected and significant improvements in callability of one or more of fosmid promoter regions, High GC, Huge GC, Low GC, High AT, Huge AT, and AT dinucleotide repeat regions, compared to that of the control.

Example 3

Evaluation of Mutants Having Mutations Homologous to P321K and D334K Double Mutants The performance of recombinase mutants having mutations homologous to P321K and D334K is evaluated. In this example, "control" recombinases are generated by modifying the wild type recombinase to comprise a mutation homologous to the H63S in RB49, as set forth in the "control" column in the table below. The "P321K D334K homolog" mutants are generated by further modifying the controls to bear a mutation homologous to P321K and D334K in RB49 as set forth in the "P321K D334K homolog" column in Table 4 below.

It will be appreciated that, as evidenced in FIG. 1, cyanophage P-SSM2, cyanophage PSSM4, and cyanophage S-PM2 do not have regions homologous to RB49 Pro321. Thus, although the mutants shown in the table below are referred to as "double mutants," only certain recombinases comprise two mutations to the control backbone.

For example, for T6 UvsX, the control is generated by modifying wild type T6 UvsX (SEQ ID NO: 9) to bear a H66S mutation. The P321K D334K homolog is further modified to bear H66S, P324K and R337K mutations.

TABLE 4

| WT backbone | WT backbone SEQ ID NO: | Control | P321K D334K homolog |
|---|---|---|---|
| RB49 | 1 | H63S | H63S P321K D334K |
| T4 | 8 | 64S | 64S P322K R335 |
| T6 | 9 | H66S | H66S P324K R337 |
| Acinetobacter phage 133 | 10 | H64S | H64S P320K T333 |
| Rb69 | 11 | H64S | H64S P323K T336 |
| Aeh1 | 12 | H76S | H76S P334K D347 |
| Aeromonas phage 65 | 13 | H73S | H73S P333K N346 |
| KVP40 | 14 | H64S | H64S D332K R345 |
| Rb43 | 15 | H66S | H66S P324K D337 |
| cyanophage P-SSM2 | 16 | T62S | T62S E328 |
| cyanophage PSSM4 | 17 | T65S | T65S K330 |
| cyanophage S-PM2 | 18 | T65S | T65S R331 |
| Rb32 | 19 | H66S | H66S P324K R337 |
| Vibrio phage nt-1 | 20 | H64S | H64S E332K R345 |
| Rb16 | 21 | H66S | H66S P324K D337 |

Clustering of a PCR-free library on a patterned flow cell is performed on a cBot as described in Example 1 above, using either control or P321K D334K mutant. Sequencing is then performed on a HiSeq instrument (Illumina, Inc.) and the sequencing results are analyzed as described in Example 1 above to determine callability of a variety of regions which are typically poorly represented in previous sequencing data.

A comparison of callability data for control vs. P321K D334K homolog mutants demonstrates that the P321K D334K homolog mutants show unexpected and significant improvements in callability of one or more of fosmid promoter regions, High GC, Huge GC, Low GC, High AT, Huge AT, and AT dinucleotide repeat regions, compared to that of the control.

Example 4

Evaluation of Mutants Having Mutations Homologous to P256K P321K and D334K Triple Mutants The performance of recombinase mutants having mutations homologous to P256K, P321K and D334K is evaluated. In this example, "control" recombinases are generated by modifying the wild type recombinase to comprise a mutation homologous to the H63S in RB49, as set forth in the "control" column in the table below. The "P256K P321K D334K homolog" triple mutants are generated by further modifying the controls to bear a mutation homologous to P256K, P321K and D334K in RB49 as set forth in the "P256K P321K D334K homolog" column in the table below.

It will be appreciated that, as evidenced in FIG. 1, cyanophage P-SSM2, cyanophage PSSM4, and cyanophage S-PM2 do not have regions homologous to RB49 Pro321. Thus, although the mutants shown in Table 5 below are referred to as "triple mutants," only certain recombinases comprise three mutations to the control backbone.

For example, for T6 UvsX, the control is generated by modifying wild type T6 UvsX (SEQ ID NO: 9) to bear a H66S mutation. The P321K D334K homolog is further modified to bear H66S, F259K, P324K and R337K mutations.

TABLE 5

| WT backbone | WT backbone SEQ ID NO: | Control | P256K P321K D334K homolog |
|---|---|---|---|
| RB49 | 1 | H63S | H63S P256K P321K D334K |
| T4 | 8 | 64S | 64S F257K P322K R335 |
| T6 | 9 | H66S | H66S F259K P324K R337 |
| Acinetobacter phage 133 | 10 | H64S | H64S P257K P320K T333 |
| Rb69 | 11 | H64S | H64S P258K P323K T336 |
| Aeh1 | 12 | H76S | H76S P269K P334K D347 |
| Aeromonas phage 65 | 13 | H73S | H73S D266K P333K N346 |
| KVP40 | 14 | H64S | H64S P267K D332K R345 |
| Rb43 | 15 | H66S | H66S P259K P324K D337 |
| cyanophage P-SSM2 | 16 | T62S | T62S Q261K E328 |
| cyanophage PSSM4 | 17 | T65S | T65S K330 |
| cyanophage S-PM2 | 18 | T65S | T65S E264K R331 |
| Rb32 | 19 | H66S | H66S P324K R337 |
| Vibrio phage nt-1 | 20 | H64S | H64S F259K E332K R345 |
| Rb16 | 21 | H66S | H66S P259K P324K D337 |

Clustering of a PCR-free library on a patterned flow cell is performed on a cBot as described in Example 1 above, using either control or P256K P321K D334K triple mutant. Sequencing is then performed on a HiSeq instrument (Illumina, Inc.) and the sequencing results are analyzed as described in Example 1 above to determine callability of a variety of regions which are typically poorly represented in previous sequencing data.

A comparison of callability data for control vs. P256K P321K D334K homolog triple mutants demonstrates that the P256K P321K D334K homolog mutants show unexpected and significant improvements in callability of one or more of fosmid promoter regions, High GC, Huge GC, Low GC, High AT, Huge AT, and AT dinucleotide repeat regions, compared to that of the control.

Example 5

Clustering with H63S P256K and H63S P321K D334K of RB49 UvsX

The performance of recombinase mutants H63 S P256K in RB49 UvsX and H63S P321K D334K in RB49 Uv was evaluated. Clustering of a PCR-free library on a patterned flow cell was performed on a cBot as described in Examples 1 to 4 above. Sequencing is then performed on a HiSeq instrument (Illumina, Inc.) and the sequencing results are analyzed as described in Examples 1 to 4 above to determine callability of a variety of regions which are typically poorly represented in previous sequencing data.

FIG. 3 shows typhoon images of 150 pM Human PCR-free libraries clustered with V2 chemistry on 700 nM pitch v2.5 pFC. 1st cycle DNA sequencing was imaged on a typhoon scanner measuring green fluorescence (G or T incorporation) and red fluorescence (A or C incorporation). Lane assignments are as follows. Briefly, lane 1 is H63S P256K. Lane 2 is H63S P321K D334K in buffer 1. Lane 3 is H63S P321K D334K in buffer 2. Lane 4 is Wt RB69 UvsX. Lane 5 is H63S P256K. Lane 6 is H63S P321K D334K in buffer 1. Lane 7 is H63S P321K D334K in buffer 2. Lane 8 is with no DNA. Buffer 1 is 20 mM Tris pH 7.5, 200 mM NaCl, 1 mM EDTA, and 1 mM BME. Buffer 2 is 50 mM Tris PH 7.5, 100 mM NaCL, 1 mM DTT, 0.1 mM EDTA, and 50% Glycerol.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may

SEQUENCE LISTING FREE TEXT

SEQ ID NO:1 Enterobacteria phage RB49 UvsX amino acid sequence
SEQ ID NO:2 Amino acid sequence Enterobacteria phage RB49 UvsX mutant comprising His63Ser (H63S) and Pro321Lys (P321K) mutations
SEQ ID NO:3 Semi Conserved Domain corresponding to amino acid residues 319 to 323 of Enterobacteria phage T4 UvsX
SEQ ID NO:4 Variants of Semi Conserved Domain 319 to 323 of Enterobacteria phage T4 UvsX
SEQ ID NO:5 Semi Conserved Domain corresponding to amino acid residues 332 to 337 of Enterobacteria phage T4 UvsX
SEQ ID NO:6 Variants of Semi Conserved Domain 319 to 323 of Enterobacteria phage T4 UvsX
SEQ ID NO:7 Variants of Semi Conserved Domain 329 to 337 of Enterobacteria phage T4 UvsX
SEQ ID NO:8 Enterobacteria phage T4 UvsX amino acid sequence
SEQ ID NO:9 Enterobacteria phage T6 UvsX amino acid sequence
SEQ ID NO:10 *Acinetobacter* phage 133 UvsX amino acid sequence
SEQ ID NO:11 Enterobacteria phage RB69 UvsX amino acid sequence
SEQ ID NO:12 *Aeromonas* phage Aeh1 UvsX amino acid sequence
SEQ ID NO:13 *Aeromonas* phage 65 UvsX amino acid sequence
SEQ ID NO:14 *Vibrio* phage KVP40 UvsX amino acid sequence
SEQ ID NO:15 Enterobacteria phage RB43 UvsX amino acid sequence
SEQ ID NO:16 *Prochlorococcus* phage P-SSM2 UvsX amino acid sequence
SEQ ID NO:17 *Prochlorococcus* phage P-SSM4 UvsX amino acid sequence
SEQ ID NO:18 *Synechococcus* phage S-PM2 UvsX amino acid sequence
SEQ ID NO:19 Enterobacteria phage RB32 UvsX amino acid sequence
SEQ ID NO:20 *Vibrio* phage nt-1 UvsX amino acid sequence
SEQ ID NO:21 Enterobacteria phage RB16 UvsX amino acid sequence
SEQ ID NO:22 Amino acid sequence Enterobacteria phage T4 UvsX mutant with Phe257Lys (F257K) mutation
SEQ ID NO:23 Amino acid sequence Enterobacteria phage T6 UvsX mutant with Phe259Lys (F259K) mutation
SEQ ID NO:24 Amino acid sequence *Acinetobacter* phage 133 UvsX mutant with Pro257Lys (P257K) mutation
SEQ ID NO:25 Amino acid sequence Enterobacteria phage RB69 UvsX mutant with Pro258Lys (P258K) mutation
SEQ ID NO:26 Amino acid sequence *Aeromonas* phage Aeh1 UvsX mutant with Pro269Lys (P269K) mutation
SEQ ID NO:27 Amino acid sequence *Aeromonas* phage 65 UvsX mutant with Asp266Lys (D266K) mutation
SEQ ID NO:28 Amino acid sequence *Vibrio* phage KVP40UvsX mutant with Pro267Lys (P266K) mutation
SEQ ID NO:29 Amino acid sequence Enterobacteria phage RB43 UvsX mutant with Pro259Lys (P259K) mutation
SEQ ID NO:30 Amino acid sequence *Prochlorococcus* phage P-SSM2 UvsX mutant with Gln261Lys (Q261K) mutation
SEQ ID NO:31 Amino acid sequence *Prochlorococcus* phage P-SSM4 UvsX mutant with Glu264Lys (E264K) mutation
SEQ ID NO:32 Amino acid sequence *Synechococcus* phage S-PM2 UvsX mutant with Glu264Lys (E264K) mutation
SEQ ID NO:33 Amino acid sequence Enterobacteria phage RB32 UvsX mutant with Phe259Lys (F259K) mutation
SEQ ID NO:34 Amino acid sequence *Vibrio* phage nt-1 UvsX mutant with Pro267Lys (P267K) mutation
SEQ ID NO:35 Amino acid sequence Enterobacteria phage RB16 UvsX mutant with Pro259Lys (P259K) mutation
SEQ ID NO:36 Semi Conserved Domain corresponding to amino acid residues 329 to 337 of Enterobacteria phage T4 UvsX

What is claimed is:

1. A UvsX recombinase polypeptide comprising an amino acid sequence that is at least 95% identical to the amino acid sequence SEQ ID NO: 1, wherein said UvsX recombinase polypeptide comprises at least one amino acid substitution mutation at a position corresponding to position Pro321 and/or position Asp334 in the RB49 UvsX amino acid sequence SEQ ID NO:1, and wherein said UvsX recombinase polypeptide demonstrates recombinase activity.

2. The UvsX recombinase polypeptide of claim 1, said UvsX recombinase polypeptide having increased recombinase activity compared to a RB49 UvsX recombinase polypeptide having the amino acid sequence of SEQ ID NO:1 with a His to Ser substitution at amino acid position 63 of SEQ ID NO:1.

3. The UvsX recombinase polypeptide of claim 2, wherein said recombinase activity is increased in the presence of a single stranded template nucleic acid compared to a RB49 UvsX recombinase polypeptide having the amino acid sequence of SEQ ID NO:1 with a His to Ser substitution at amino acid position 63 of SEQ ID NO:1.

4. The UvsX recombinase polypeptide of claim 2, said UvsX recombinase polypeptide having improved seeding and/or amplification on a solid support compared to a RB49 UvsX recombinase polypeptide having the amino acid sequence of SEQ ID NO:1 with a His to Ser substitution at amino acid position 63 of SEQ ID NO:1.

5. A UvsX recombinase polypeptide comprising SEQ ID NO:2 with an Asp334Lys substitution and/or a Pro256Lys substitution in the amino acid sequence of SEQ ID NO:2.

6. The UvsX recombinase polypeptide of claim 1, wherein the UvsX recombinase polypeptide comprises an amino acid sequence that is at least 99% identical to SEQ ID NO: 1.

7. The UvsX recombinase polypeptide of claim 1, wherein the at least one substitution mutation comprises a mutation to a charged residue.

8. The UvsX recombinase polypeptide of claim 1, wherein the at least one substitution mutation comprises a mutation to a basic residue.

9. The UvsX recombinase polypeptide of claim 1, wherein the at least one substitution mutation at a position corresponding to position Pro321 in the RB49 UvsX amino acid sequence SEQ ID NO:1 comprises a Pro321Lys substitution mutation.

10. The UvsX recombinase polypeptide of claim 1, wherein the at least one substitution mutation at a position corresponding to position Asp334 in the RB49 UvsX amino acid sequence SEQ ID NO:1 comprises a Asp334Lys substitution mutation.

11. The UvsX recombinase polypeptide of claim 1, wherein the at least one substitution mutation corresponding to positions Pro321 and Asp334 in the RB49 UvsX amino acid sequence SEQ ID NO:1 comprises Pro321Lys and Asp334Lys substitution mutations.

12. The UvsX recombinase polypeptide of claim 1, further comprising a substitution mutation at a position corresponding to Pro256 in the RB49 UvsX amino acid sequence SEQ ID NO:1.

13. The UvsX recombinase polypeptide of claim 12, wherein the substitution mutation at a position corresponding to Pro256 in the RB49 UvsX amino acid sequence SEQ ID NO:1 comprises a Pro256Lys substitution mutation.

14. The UvsX recombinase polypeptide of claim 1, further comprising a substitution mutation at a position corresponding to His63 in the RB49 UvsX amino acid sequence SEQ ID NO:1.

15. The UvsX recombinase polypeptide of claim 14, wherein the substitution mutation at a position corresponding to His63 in the RB49 UvsX amino acid sequence SEQ ID NO:1 comprises a His63 Ser substitution mutation.

16. The UvsX recombinase polypeptide of claim 1, further comprising a mutation selected from the group consisting of: the addition of one or more glutamic acid residues at the C-terminus, the addition of one or more aspartic acid residues at the C-terminus, and a combination thereof.

17. The UvsX recombinase polypeptide of claim 1, comprising the amino acid sequence of SEQ ID NO: 2.

18. A UvsX recombinase polypeptide comprising the amino acid sequence of SEQ ID NO:2 with a substitution mutation at position Pro256 of SEQ ID NO:2.

19. The UvsX recombinase polypeptide of claim 18, wherein the substitution mutation at position Pro256 comprises a Pro256Lys substitution mutation in the amino acid sequence SEQ ID NO:2.

20. The UvsX recombinase polypeptide of claim 1, comprising amino acid substitution mutations at the positions corresponding to positions Pro321 and Asp334 in the RB49 amino acid sequence SEQ ID NO: 1.

* * * * *

SEQUENCE LISTING

```
<160> NUMBER OF SEQ ID NOS: 36

<210> SEQ ID NO 1
<211> LENGTH: 356
<212> TYPE: PRT
<213> ORGANISM: Enterobacteria phage RB49

<400> SEQUENCE: 1

Met Ser Val Leu Glu Lys Leu Lys Lys Asn Ser Thr Leu Lys Thr Thr
1               5                   10                  15

Ala Val Leu Ser Lys Ser Ser Phe Phe Asn Glu Lys Thr Asn Thr Arg
            20                  25                  30

Thr Lys Ile Pro Met Leu Asn Ile Ala Phe Ser Gly Asp Leu Lys Lys
        35                  40                  45

Gly Phe Gln Ser Gly Leu Ile Phe Phe Ala Gly Pro Ser Lys His Phe
    50                  55                  60

Lys Ser Asn Met Gly Leu Thr Cys Val Ser Ala Tyr Met Lys Gln Asn
65                  70                  75                  80

Pro Asp Ala Ala Cys Leu Phe Phe Asp Ser Glu Phe Gly Ile Thr Ser
```

```
            85              90              95
Ala Tyr Leu Glu Ser Met Gly Val Asp Pro Arg Val His Val
            100             105             110

Pro Ile Lys Asn Ile Glu Glu Leu Lys Phe Glu Ile Met Asn Gln Leu
            115             120             125

Glu Gln Ile Thr Arg Glu Asp Lys Val Ile Ile Phe Ile Asp Ser Ile
130             135             140

Gly Asn Leu Ala Ser Lys Lys Glu Val Glu Asp Ala Ile Asn Glu Lys
145             150             155             160

Ser Ala Gln Asp Met Thr Arg Ala Lys Ala Leu Lys Gly Leu Phe Arg
                165             170             175

Met Val Thr Pro Tyr Leu Thr Met Asn Asp Ile Pro Cys Ile Ala Ile
            180             185             190

Asn His Thr Tyr Glu Thr Gln Glu Met Phe Ser Lys Thr Val Met Ser
            195             200             205

Gly Gly Thr Gly Ala Met Tyr Ser Ala Asn Glu Val Phe Ile Ile Gly
            210             215             220

Arg Arg Gln Gln Lys Glu Gly Thr Glu Ile Thr Gly Tyr Asp Phe Ile
225             230             235             240

Leu Asn Ala Glu Lys Ser Arg Thr Val Lys Glu Lys Ser Lys Phe Pro
                245             250             255

Ile Ser Val Thr Phe Ser Gly Gly Ile Asp Pro Tyr Ser Gly Leu Leu
            260             265             270

Glu Leu Ala Val Glu Leu Gly Trp Val Val Lys Pro Ser Asn Gly Trp
            275             280             285

Tyr Ser Arg Ser Ile Leu Asn Thr Glu Thr Gly Glu Met Glu Thr Glu
            290             295             300

Glu Arg Lys Phe Arg Ala Lys Glu Thr Asn Ser Ile Glu Phe Trp Lys
305             310             315             320

Pro Leu Leu Thr Asn Asp Lys Phe Asn Glu Ala Ile Asn Asp His Tyr
                325             330             335

Lys Leu Gly Gln Val Ile Ser Asp Glu Ala Val Asp Lys Glu Ile Glu
            340             345             350

Asp Met Leu Ala
            355

<210> SEQ ID NO 2
<211> LENGTH: 356
<212> TYPE: PRT
<213> ORGANISM: Enterobacteria phage RB49

<400> SEQUENCE: 2

Met Ser Val Leu Glu Lys Leu Lys Lys Asn Ser Thr Leu Lys Thr Thr
1               5               10              15

Ala Val Leu Ser Lys Ser Ser Phe Asn Glu Lys Thr Asn Thr Arg
            20              25              30

Thr Lys Ile Pro Met Leu Asn Ile Ala Phe Ser Gly Asp Leu Lys Lys
            35              40              45

Gly Phe Gln Ser Gly Leu Ile Phe Phe Ala Gly Pro Ser Lys Ser Phe
        50              55              60

Lys Ser Asn Met Gly Leu Thr Cys Val Ser Ala Tyr Met Lys Gln Asn
65              70              75              80

Pro Asp Ala Ala Cys Leu Phe Phe Asp Ser Glu Phe Gly Ile Thr Ser
            85              90              95
```

```
Ala Tyr Leu Glu Ser Met Gly Val Asp Pro Asp Arg Val His Val
                100                 105                 110

Pro Ile Lys Asn Ile Glu Glu Leu Lys Phe Glu Ile Met Asn Gln Leu
        115                 120                 125

Glu Gln Ile Thr Arg Glu Asp Lys Val Ile Ile Phe Ile Asp Ser Ile
    130                 135                 140

Gly Asn Leu Ala Ser Lys Lys Glu Val Glu Asp Ala Ile Asn Glu Lys
145                 150                 155                 160

Ser Ala Gln Asp Met Thr Arg Ala Lys Ala Leu Lys Gly Leu Phe Arg
                165                 170                 175

Met Val Thr Pro Tyr Leu Thr Met Asn Asp Ile Pro Cys Ile Ala Ile
            180                 185                 190

Asn His Thr Tyr Glu Thr Gln Glu Met Phe Ser Lys Thr Val Met Ser
        195                 200                 205

Gly Gly Thr Gly Ala Met Tyr Ser Ala Asn Glu Val Phe Ile Ile Gly
    210                 215                 220

Arg Arg Gln Gln Lys Glu Gly Thr Glu Ile Thr Gly Tyr Asp Phe Ile
225                 230                 235                 240

Leu Asn Ala Glu Lys Ser Arg Thr Val Lys Glu Lys Ser Lys Phe Pro
                245                 250                 255

Ile Ser Val Thr Phe Ser Gly Gly Ile Asp Pro Tyr Ser Gly Leu Leu
            260                 265                 270

Glu Leu Ala Val Glu Leu Gly Trp Val Lys Pro Ser Asn Gly Trp
        275                 280                 285

Tyr Ser Arg Ser Ile Leu Asn Thr Glu Thr Gly Glu Met Glu Thr Glu
290                 295                 300

Glu Arg Lys Phe Arg Ala Lys Glu Thr Asn Ser Ile Glu Phe Trp Lys
305                 310                 315                 320

Lys Leu Leu Thr Asn Asp Lys Phe Asn Glu Ala Ile Asn Asp His Tyr
                325                 330                 335

Lys Leu Gly Gln Val Ile Ser Asp Glu Ala Val Asp Lys Glu Ile Glu
            340                 345                 350

Asp Met Leu Ala
        355

<210> SEQ ID NO 3
<211> LENGTH: 5
<212> TYPE: PRT
<213> ORGANISM: Artificial Sequence
<220> FEATURE:
<223> OTHER INFORMATION: Semi Conserved Domain

<400> SEQUENCE: 3

Phe Trp Gly Pro Leu
1               5

<210> SEQ ID NO 4
<211> LENGTH: 6
<212> TYPE: PRT
<213> ORGANISM: Artificial Sequence
<220> FEATURE:
<223> OTHER INFORMATION: Semi Conserved Domain
<220> FEATURE:
<221> NAME/KEY: VARIANT
<222> LOCATION: (3)..(3)
<223> OTHER INFORMATION: X = G, K, R
<220> FEATURE:
<221> NAME/KEY: VARIANT
<222> LOCATION: (4)..(4)
<223> OTHER INFORMATION: X = P, D
```

```
<220> FEATURE:
<221> NAME/KEY: VARIANT
<222> LOCATION: (5)..(5)
<223> OTHER INFORMATION: X = L, M, I
<220> FEATURE:
<221> NAME/KEY: VARIANT
<222> LOCATION: (6)..(6)
<223> OTHER INFORMATION: X = F, L, I

<400> SEQUENCE: 4

Phe Trp Xaa Xaa Xaa Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Semi Conserved Domain

<400> SEQUENCE: 5

Ala Ile Lys Arg Ala Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Semi Conserved Domain
<220> FEATURE:
<221> NAME/KEY: VARIANT
<222> LOCATION: (3)..(3)
<223> OTHER INFORMATION: X = K, N, E
<220> FEATURE:
<221> NAME/KEY: VARIANT
<222> LOCATION: (4)..(4)
<223> OTHER INFORMATION: X = R, T, D
<220> FEATURE:
<221> NAME/KEY: VARIANT
<222> LOCATION: (5)..(5)
<223> OTHER INFORMATION: X = H, A, R, K

<400> SEQUENCE: 6

Ala Ile Xaa Xaa Xaa Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Semi Conserved Domain
<220> FEATURE:
<221> NAME/KEY: VARIANT
<222> LOCATION: (1)..(1)
<223> OTHER INFORMATION: X = F, L
<220> FEATURE:
<221> NAME/KEY: VARIANT
<222> LOCATION: (2)..(2)
<223> OTHER INFORMATION: X = R, K, M, L, N
<220> FEATURE:
<221> NAME/KEY: VARIANT
<222> LOCATION: (3)..(3)
<223> OTHER INFORMATION: X = D, K, T, E
<220> FEATURE:
<221> NAME/KEY: VARIANT
<222> LOCATION: (4)..(4)
<223> OTHER INFORMATION: X = A, G, I
<220> FEATURE:
<221> NAME/KEY: VARIANT
<222> LOCATION: (5)..(5)
<223> OTHER INFORMATION: X = I, C, V
```

```
<220> FEATURE:
<221> NAME/KEY: VARIANT
<222> LOCATION: (6)..(6)
<223> OTHER INFORMATION: X = K, E, S, Q, N
<220> FEATURE:
<221> NAME/KEY: VARIANT
<222> LOCATION: (7)..(7)
<223> OTHER INFORMATION: X = R, T, D, N, E, K
<220> FEATURE:
<221> NAME/KEY: VARIANT
<222> LOCATION: (8)..(8)
<223> OTHER INFORMATION: X = A, R, K, M, I, H, E
<220> FEATURE:
<221> NAME/KEY: VARIANT
<222> LOCATION: (9)..(9)
<223> OTHER INFORMATION: X = Y, F

<400> SEQUENCE: 7

Xaa Xaa Xaa Xaa Xaa Xaa Xaa Xaa Xaa
1               5

<210> SEQ ID NO 8
<211> LENGTH: 391
<212> TYPE: PRT
<213> ORGANISM: Enterobacteria phage T4

<400> SEQUENCE: 8

Met Ser Asp Leu Lys Ser Arg Leu Ile Lys Ala Ser Thr Ser Lys Leu
1               5                   10                  15

Thr Ala Glu Leu Thr Ala Ser Lys Phe Phe Asn Glu Lys Asp Val Val
            20                  25                  30

Arg Thr Lys Ile Pro Met Met Asn Ile Ala Leu Ser Gly Glu Ile Thr
        35                  40                  45

Gly Gly Met Gln Ser Gly Leu Leu Ile Leu Ala Gly Pro Ser Lys Ser
    50                  55                  60

Phe Lys Ser Asn Phe Gly Leu Thr Met Val Ser Ser Tyr Met Arg Gln
65                  70                  75                  80

Tyr Pro Asp Ala Val Cys Leu Phe Tyr Asp Ser Glu Phe Gly Ile Thr
                85                  90                  95

Pro Ala Tyr Leu Arg Ser Met Gly Val Asp Pro Glu Arg Val Ile His
            100                 105                 110

Thr Pro Val Gln Ser Leu Glu Gln Leu Arg Ile Asp Met Val Asn Gln
        115                 120                 125

Leu Asp Ala Ile Glu Arg Gly Glu Lys Val Val Phe Ile Asp Ser
    130                 135                 140

Leu Gly Asn Leu Ala Ser Lys Lys Glu Thr Glu Asp Ala Leu Asn Glu
145                 150                 155                 160

Lys Val Val Ser Asp Met Thr Arg Ala Lys Thr Met Lys Ser Leu Phe
                165                 170                 175

Arg Ile Val Thr Pro Tyr Phe Ser Thr Lys Asn Ile Pro Cys Ile Ala
            180                 185                 190

Ile Asn His Thr Tyr Glu Thr Gln Glu Met Phe Ser Lys Thr Val Met
        195                 200                 205

Gly Gly Gly Thr Gly Pro Met Tyr Ser Ala Asp Thr Val Phe Ile Ile
    210                 215                 220

Gly Lys Arg Gln Ile Lys Asp Gly Ser Asp Leu Gln Gly Tyr Gln Phe
225                 230                 235                 240

Val Leu Asn Val Glu Lys Ser Arg Thr Val Lys Glu Lys Ser Lys Phe
                245                 250                 255

Phe Ile Asp Val Lys Phe Asp Gly Gly Ile Asp Pro Tyr Ser Gly Leu
```

```
                  260                 265                 270
Leu Asp Met Ala Leu Glu Leu Gly Phe Val Lys Pro Lys Asn Gly
                275                 280                 285

Trp Tyr Ala Arg Glu Phe Leu Asp Glu Glu Thr Gly Glu Met Ile Arg
                290                 295                 300

Glu Glu Lys Ser Trp Arg Ala Lys Asp Thr Asn Cys Thr Thr Phe Trp
305                 310                 315                 320

Gly Pro Leu Phe Lys His Gln Pro Phe Arg Asp Ala Ile Lys Arg Ala
                325                 330                 335

Tyr Gln Leu Gly Ala Ile Asp Ser Asn Glu Ile Val Glu Ala Glu Val
                340                 345                 350

Asp Glu Leu Ile Asn Ser Lys Val Glu Lys Phe Lys Ser Pro Glu Ser
                355                 360                 365

Lys Ser Lys Ser Ala Ala Asp Leu Glu Thr Asp Leu Glu Gln Leu Ser
                370                 375                 380

Asp Met Glu Glu Phe Asn Glu
385                 390

<210> SEQ ID NO 9
<211> LENGTH: 393
<212> TYPE: PRT
<213> ORGANISM: Enterobacteria phage T6

<400> SEQUENCE: 9

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
                20                  25                  30

Val Ile Arg Thr Lys Ile Pro Met Leu Asn Ile Ala Ile Ser Gly Ala
            35                  40                  45

Ile Asp Gly Gly Met Gln Ser Gly Leu Thr Ile Phe Ala Gly Pro Ser
        50                  55                  60

Lys His Phe Lys Ser Asn Met Ser Leu Thr Met Val Ala Ala Tyr Leu
65              70                  75                  80

Asn Lys Tyr Pro Asp Ala Val Cys Leu Phe Tyr Asp Ser Glu Phe Gly
                85                  90                  95

Ile Thr Pro Ala Tyr Leu Arg Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Ala Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220

Ile Ile Gly Lys Arg Gln Ile Lys Asp Gly Ser Asp Leu Gln Gly Tyr
225                 230                 235                 240
```

```
Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Glu Thr Gly Glu Met
    290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
        355                 360                 365

Glu Ser Lys Ser Lys Ser Ala Ala Asp Leu Glu Thr Asp Leu Glu Gln
    370                 375                 380

Leu Ser Asp Met Glu Glu Phe Asn Glu
385                 390

<210> SEQ ID NO 10
<211> LENGTH: 387
<212> TYPE: PRT
<213> ORGANISM: Acinetobacter phage 133

<400> SEQUENCE: 10

Met Ser Ser Leu Lys Glu Arg Leu Ile Lys Ala Ser Thr Ser Lys Met
1               5                   10                  15

Thr Ala Glu Leu Thr Lys Ser Lys Phe Phe Asn Asp Lys Thr Val Val
            20                  25                  30

Arg Thr Arg Ile Pro Met Leu Asn Ile Ala Ile Ser Gly Ala Leu Asn
        35                  40                  45

Gly Gly Met Gln Ser Gly Leu Thr Ile Phe Ala Gly Pro Ser Lys His
    50                  55                  60

Phe Lys Ser Asn Met Gly Leu Thr Met Val Ala Ala Tyr Met Lys Ala
65                  70                  75                  80

Phe Pro Asp Ala Val Cys Met Phe Tyr Asp Ser Glu Phe Gly Ile Thr
                85                  90                  95

Pro Ala Tyr Leu Lys Ala Met Gly Val Asp Pro Asp Arg Val Ile His
            100                 105                 110

Thr Pro Val Gln Ser Val Glu Gln Leu Lys Ile Asp Met Thr Asn Gln
        115                 120                 125

Leu Glu Glu Val Lys Arg Gly Glu Lys Val Ile Val Phe Ile Asp Ser
    130                 135                 140

Ile Gly Asn Leu Ala Ser Lys Lys Glu Thr Glu Asp Ala Leu Asn Glu
145                 150                 155                 160

Lys Thr Thr Ala Asp Met Thr Arg Ala Lys Ala Leu Lys Ser Leu Phe
                165                 170                 175

Arg Ile Val Thr Pro Tyr Phe Ser Ile Lys Asp Ile Pro Cys Val Ala
            180                 185                 190

Val Asn His Thr Leu Gln Thr Leu Glu Met Phe Ser Lys Glu Val Met
        195                 200                 205

Thr Gly Gly Thr Gly Val Met Tyr Ser Ala Asp Thr Val Phe Phe Ile
    210                 215                 220
```

```
Gly Lys Arg Gln Val Lys Asp Gly Thr Glu Leu Ala Gly Tyr Glu Phe
225                 230                 235                 240

Ile Leu Lys Ala Glu Lys Ser Arg Met Val Lys Glu Lys Ser Val Phe
                245                 250                 255

Pro Ile Thr Val Lys Phe Asp Gly Gly Ile Asp Pro Tyr Ser Gly Leu
            260                 265                 270

Leu Glu Met Ala Thr Asp Leu Gly Phe Val Val Lys Pro Lys Val Gly
        275                 280                 285

Trp Tyr Lys Arg Ala Met Met Val Asp Gly Val Met Gln His Glu Glu
    290                 295                 300

Lys Ser Trp Arg Ala Lys Asp Thr Asp Ser Ile Asp Phe Trp Gly Pro
305                 310                 315                 320

Leu Phe Lys His Asp Glu Phe Arg Lys Ala Ile Glu Thr Arg Tyr Gln
                325                 330                 335

Leu Gly Ser Ile Glu Ser Asp Ala Glu Val Asp Ala Glu Val Asp Ala
            340                 345                 350

Leu Ile Gly Ser Lys Thr Thr Ala Lys Ile Ser Gly Val Asn Phe Gly
        355                 360                 365

Pro Ala Glu Ser Ala Ala Asp Lys Glu Gln Gln Leu Gly Asp Phe Val
    370                 375                 380

Asp Glu Asp
385

<210> SEQ ID NO 11
<211> LENGTH: 390
<212> TYPE: PRT
<213> ORGANISM: Enterobacteria phage RB69

<400> SEQUENCE: 11

Met Ser Asp Leu Lys Ser Arg Leu Ile Lys Ala Ser Thr Ser Lys Met
1               5                   10                  15

Thr Ala Asp Leu Thr Lys Ser Lys Leu Phe Asn Asn Arg Asp Glu Val
            20                  25                  30

Pro Thr Arg Ile Pro Met Leu Asn Ile Ala Leu Gly Gly Ala Leu Asn
        35                  40                  45

Ala Gly Leu Gln Ser Gly Leu Thr Ile Phe Ala Ala Pro Ser Lys His
    50                  55                  60

Phe Lys Thr Leu Phe Gly Leu Thr Met Val Ala Ala Tyr Met Lys Lys
65                  70                  75                  80

Tyr Lys Asp Ala Ile Cys Leu Phe Tyr Asp Ser Glu Phe Gly Ala Ser
                85                  90                  95

Glu Ser Tyr Phe Arg Ser Met Gly Val Asp Leu Asp Arg Val Val His
            100                 105                 110

Thr Pro Ile Gln Ser Val Glu Gln Leu Lys Val Asp Met Thr Asn Gln
        115                 120                 125

Leu Asp Ala Ile Glu Arg Gly Asp Lys Val Ile Phe Ile Asp Ser
    130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
            180                 185                 190

Ile Asn His Thr Ala Met Glu Ile Gly Gly Leu Tyr Pro Lys Glu Ile
```

```
              195                 200                 205
Met Gly Gly Gly Thr Gly Ile Leu Tyr Ser Ala Asn Thr Val Phe Phe
210                 215                 220

Ile Ser Lys Arg Gln Val Lys Glu Gly Thr Glu Leu Thr Gly Tyr Asp
225                 230                 235                 240

Phe Thr Leu Lys Ala Glu Lys Ser Arg Thr Val Lys Glu Lys Ser Thr
                245                 250                 255

Phe Pro Ile Thr Val Asn Phe Asp Gly Ile Asp Pro Phe Ser Gly
                260                 265                 270

Leu Leu Glu Met Ala Thr Glu Ile Gly Phe Val Val Lys Pro Lys Ala
            275                 280                 285

Gly Trp Tyr Ala Arg Glu Phe Leu Asp Glu Glu Thr Gly Glu Met Ile
            290                 295                 300

Arg Glu Glu Lys Ser Trp Arg Ala Lys Ala Thr Asp Cys Val Glu Phe
305                 310                 315                 320

Trp Gly Pro Leu Phe Lys His Lys Pro Phe Arg Asp Ala Ile Glu Thr
                325                 330                 335

Lys Tyr Lys Leu Gly Ala Ile Ser Ser Ile Lys Glu Val Asp Asp Ala
                340                 345                 350

Val Asn Asp Leu Ile Asn Cys Lys Ala Thr Thr Lys Val Pro Val Lys
            355                 360                 365

Thr Ser Asp Ala Pro Ser Ala Ala Asp Ile Glu Asn Asp Leu Asp Glu
            370                 375                 380

Met Glu Asp Phe Asp Glu
385                 390

<210> SEQ ID NO 12
<211> LENGTH: 411
<212> TYPE: PRT
<213> ORGANISM: Aeromonas phage Aeh1

<400> SEQUENCE: 12

Met Ala Lys Gly Ile Lys Thr Ala Lys Thr Gly Asn Leu Gly Ser Leu
1               5                   10                  15

Met Ser Lys Leu Ala Gly Thr Ser Asn Lys Met Ser Ser Val Leu
                20                  25                  30

Ala Asp Ser Lys Phe Phe Asn Asp Lys Asp Cys Val Arg Thr Arg Val
            35                  40                  45

Pro Leu Leu Asn Leu Ala Met Ser Gly Glu Leu Asp Gly Gly Leu Thr
50                  55                  60

Pro Gly Leu Thr Val Leu Ala Gly Pro Ser Lys His Phe Lys Ser Asn
65                  70                  75                  80

Leu Ser Leu Val Phe Val Ala Ala Tyr Leu Arg Lys Tyr Pro Asp Ala
                85                  90                  95

Val Cys Ile Phe Phe Asp Asn Glu Phe Gly Ser Thr Pro Gly Tyr Phe
                100                 105                 110

Glu Ser Gln Gly Val Asp Ile Ser Arg Val Ile His Cys Pro Phe Lys
            115                 120                 125

Asn Ile Glu Glu Leu Lys Phe Asp Ile Val Lys Lys Leu Glu Ala Ile
130                 135                 140

Glu Arg Gly Asp Arg Val Ile Val Phe Val Asp Ser Ile Gly Asn Ala
145                 150                 155                 160

Ala Ser Lys Lys Glu Ile Asp Asp Ala Ile Asp Glu Lys Ser Val Ser
                165                 170                 175
```

-continued

```
Asp Met Thr Arg Ala Lys Gln Ile Lys Ser Leu Thr Arg Met Met Thr
            180                 185                 190

Pro Tyr Leu Thr Val Asn Asp Ile Pro Ala Ile Met Val Ala His Thr
        195                 200                 205

Tyr Asp Thr Gln Glu Met Tyr Ser Lys Val Val Ser Gly Gly Thr
    210                 215                 220

Gly Ile Thr Tyr Ser Ser Asp Thr Val Ile Ile Gly Arg Gln Gln
225                 230                 235                 240

Glu Lys Asp Gly Lys Glu Leu Leu Gly Tyr Asn Phe Val Leu Asn Met
                245                 250                 255

Glu Lys Ser Arg Phe Val Lys Glu Gln Ser Lys Leu Pro Leu Glu Val
            260                 265                 270

Thr Phe Gln Gly Gly Ile Asn Thr Tyr Ser Gly Met Leu Asp Ile Ala
        275                 280                 285

Leu Glu Val Gly Phe Val Val Lys Pro Ser Asn Gly Trp Phe Ser Arg
    290                 295                 300

Ala Phe Leu Asp Glu Glu Thr Gly Glu Leu Val Glu Glu Asp Arg Lys
305                 310                 315                 320

Trp Arg Arg Ala Asp Thr Asn Cys Leu Glu Phe Trp Lys Pro Met Phe
                325                 330                 335

Ala His Gln Pro Phe Lys Thr Ala Cys Ser Asp Met Phe Lys Leu Lys
            340                 345                 350

Ser Val Ala Val Lys Asp Glu Val Phe Asp Glu Val Asp Glu Leu Phe
        355                 360                 365

Ser Gly Glu Ala Glu Met Pro Val Asn Met Gly Arg Lys Leu Asp Thr
    370                 375                 380

Ala Asp Gln Glu Glu Ile Asp Gln Leu Glu Glu Val Asp Val Glu Gly
385                 390                 395                 400

Ser Asp Ser Asp Glu Leu Phe Ala Asn Leu Asp
                405                 410
```

<210> SEQ ID NO 13
<211> LENGTH: 368
<212> TYPE: PRT
<213> ORGANISM: Aeromonas phage 65

<400> SEQUENCE: 13

```
Met Ala Lys Lys Ala Lys Val Val Asn Ser Gly Asp Leu Leu Glu Arg
1               5                   10                  15

Leu Asn Gly Thr Ser Ser Asn Lys Met Ser Ala Met Leu Ala Glu Ser
            20                  25                  30

Ile Phe Phe Asn Glu Lys Asp Thr Ile Arg Thr Arg Val Pro Ile Ile
        35                  40                  45

Asn Leu Met Met Ser Gly Arg Leu Asp Gly Ile Thr Pro Gly Leu
    50                  55                  60

Thr Cys Ile Ala Gly Pro Ser Lys His Phe Lys Ser Asn Leu Ser Leu
65                  70                  75                  80

Val Met Val Ser Ala Tyr Leu Arg Lys Tyr Pro Lys Ala Val Cys Leu
                85                  90                  95

Phe Phe Asp Asn Glu Phe Gly Ser Thr Pro Asp Tyr Phe Thr Ser Gln
            100                 105                 110

Gly Val Asp Ile Ser Arg Val Val His Cys Pro Phe Ile Asp Val Glu
        115                 120                 125

Glu Leu Lys Phe Asp Ile Val Lys Lys Leu Glu Ser Ile Thr Arg Gly
    130                 135                 140
```

```
Asp Lys Val Ile Ile Tyr Ile Asp Ser Ile Gly Asn Val Ala Ser Lys
145                 150                 155                 160

Lys Glu Leu Gln Asp Ala Lys Asp Glu Lys Ser Ala Gln Asp Met Thr
            165                 170                 175

Arg Ala Lys Gln Ile Lys Ser Leu Phe Arg Met Val Thr Pro Tyr Leu
            180                 185                 190

Thr Val Leu Asp Ile Pro Cys Ile Ala Val Asn His Thr Tyr Glu Thr
            195                 200                 205

Gln Glu Met Phe Ser Lys Thr Val Met Ser Gly Thr Gly Pro Met
        210                 215                 220

Tyr Ser Ala Asp Thr Val Ile Ile Leu Gly Lys Gln Gln Asp Lys Asp
225                 230                 235                 240

Gly Lys Glu Leu Leu Gly Tyr Asn Phe Val Met Asn Ala Glu Lys Ser
                245                 250                 255

Arg Ala Ile Lys Glu Lys Ser Lys Leu Asp Leu Met Val Ser Phe Glu
            260                 265                 270

Gly Gly Ile Asn Thr Tyr Ser Gly Leu Leu Lys Ile Ala Gln Glu Leu
            275                 280                 285

Gly Phe Val Thr Lys Pro Gln Asn Ala Arg Tyr Gln Arg Asn Phe Leu
        290                 295                 300

Asp Leu Glu Pro Gly Glu Met Val Ile Pro Glu Asp Glu Lys Lys Trp
305                 310                 315                 320

Thr Glu Glu Glu Ser Asp Ser Leu Glu Phe Trp Lys Pro Met Phe Ser
                325                 330                 335

His Lys Pro Phe Met Asp Ala Val Ser Asn Ala Tyr Lys Leu Lys Ala
            340                 345                 350

Val Glu Val Ser Gln Glu Val Phe Asp Glu Val Asp Gln Leu Phe Gly
            355                 360                 365

<210> SEQ ID NO 14
<211> LENGTH: 366
<212> TYPE: PRT
<213> ORGANISM: Vibrio phage KVP40

<400> SEQUENCE: 14

Met Ser Asp Leu Met Lys Ser Leu Lys Lys Ser Ser Thr Ser Gly Tyr
1               5                   10                  15

Ala Gln Val Leu Ser Glu Ser Gln Phe Met Phe Asp Lys Asp His Thr
            20                  25                  30

Arg Thr Tyr Val Pro Ala Ile Asn Ile Ala Phe Ser Gly Glu Val Asp
        35                  40                  45

Gly Gly Leu Thr Ser Gly Leu Thr Val Leu Ala Gly Pro Ser Lys His
    50                  55                  60

Phe Lys Ser Asn Leu Gly Leu Val Gly Val Ala Ala Tyr Leu Lys Lys
65                  70                  75                  80

Tyr Pro Asp Ala Val Cys Val Phe Ile Asp Thr Glu Phe Gly Ile Thr
                85                  90                  95

Pro Ser Tyr Leu Arg Ser Gln Gly Val Asp Pro Asp Arg Val Leu His
            100                 105                 110

Ile Gln Cys Glu Ser Val Glu Arg Met Lys Phe Glu Met Ala Asn Gln
        115                 120                 125

Leu Lys Asp Leu Ala Glu Arg Lys Arg Ala Lys Lys Ala Gly Glu Glu
    130                 135                 140

Pro Asp Arg Val Ile Phe Phe Ile Asp Ser Val Gly Asn Val Ala Ser
```

```
        145                 150                 155                 160
    Ala Lys Glu Ile Asp Asp Ala Gln Asn Glu Lys Ser Val Ala Asp Met
                    165                 170                 175

Ser Arg Ala Lys Gln Leu Lys Ser Leu Phe Arg Ile Ile Thr Pro Tyr
                    180                 185                 190

Phe Thr Met Leu Asp Ile Pro Cys Ile Ala Ile Asn His Thr Tyr Gln
                    195                 200                 205

Thr Gln Glu Ile Tyr Ser Lys Thr Val Met Ser Gly Thr Gly Ile
        210                 215                 220

Met Tyr Ser Ala Asp Thr Val Ile Ile Leu Gly Lys Gln Gln Glu Lys
    225                 230                 235                 240

Asp Gly Lys Asp Ile Ile Gly Tyr His Phe Ile Met Asn Ile Glu Lys
                    245                 250                 255

Ser Arg Phe Val Lys Glu Lys Met Lys Val Pro Leu Thr Val Thr Tyr
                    260                 265                 270

Glu Asn Gly Ile Asp Pro Phe Ser Gly Leu Leu Asp Ile Ala Leu Gln
                    275                 280                 285

Thr Gly His Val Val Lys Pro Ser Asn Gly Trp Tyr Gln Arg Ala Thr
        290                 295                 300

Val Asp Glu Glu Thr Gly Glu Met Ile Val Glu Lys Lys Tyr Arg
    305                 310                 315                 320

Ala Lys Glu Thr Gln Thr Ile Ser Phe Trp Lys Asp Ile Ile Asn Ser
                    325                 330                 335

Pro Thr Phe Lys Glu Gly Val Lys Arg Ile Tyr Cys Leu Gly Gln Leu
                    340                 345                 350

Asp Glu Ser Glu Leu Phe Gly Glu Val Asp Ser Leu Phe Asp
                    355                 360                 365

<210> SEQ ID NO 15
<211> LENGTH: 386
<212> TYPE: PRT
<213> ORGANISM: Enterobacteria phage RB43

<400> SEQUENCE: 15

Met Ser Asn Lys Ala Leu Leu Lys Lys Leu Ile Lys Asn Ser Asn Ser
    1               5                   10                  15

Gln Ser Ala Ala Ile Leu Ser Glu Ser Asp Val Phe Asn Asn Ile Thr
                    20                  25                  30

Lys Thr Arg Thr Arg Val Pro Ile Leu Asn Leu Ala Leu Ser Gly Ala
                    35                  40                  45

Phe Asp Gly Gly Leu Thr Ser Gly Leu Thr Leu Phe Ala Gly Pro Ser
        50                  55                  60

Lys His Phe Lys Ser Asn Leu Gly Leu Val Thr Val Ser Ala Tyr Leu
    65                  70                  75                  80

Lys Ala Asn Glu Asp Ala Val Cys Leu Phe Tyr Asp Ser Glu Lys Gly
                    85                  90                  95

Val Thr Lys Ser Tyr Leu Lys Ser Met Gly Val Asp Pro Asp Arg Val
                    100                 105                 110

Val Tyr Thr Arg Ile Thr Thr Val Glu Gln Leu Arg Asn Asp Val Val
                    115                 120                 125

Ser Gln Leu Asp Ala Leu Glu Arg Gly Asp Lys Val Ile Ile Phe Val
        130                 135                 140

Asp Ser Val Gly Asn Thr Ala Ser Lys Lys Glu Leu Ala Asp Ala Leu
    145                 150                 155                 160
```

```
Ser Asp Asn Asp Lys Gln Asp Met Thr Arg Ala Lys Ala Leu Lys Gly
            165                 170                 175

Met Phe Arg Met Val Thr Pro Tyr Leu Ala Asp Leu Asp Ile Pro Met
        180                 185                 190

Val Cys Ile Cys His Thr Tyr Asp Thr Gln Glu Met Tyr Ser Lys Lys
        195                 200                 205

Val Ile Ser Gly Gly Thr Gly Leu Met Tyr Ser Ala Asp Thr Ala Ile
        210                 215                 220

Ile Leu Gly Lys Gln Gln Val Lys Glu Gly Thr Glu Val Val Gly Tyr
225                 230                 235                 240

Asp Phe Ile Met Asn Ile Glu Lys Ser Arg Phe Val Lys Glu Lys Ser
                245                 250                 255

Lys Phe Pro Leu His Val Thr Tyr Glu Gly Gly Ile Ser Met Tyr Ser
            260                 265                 270

Gly Leu Leu Asp Leu Ala Met Glu Met Asn Phe Val Gln Thr Pro Thr
        275                 280                 285

Lys Gly Trp Arg Gly Arg Ala Phe Leu Asn Thr Glu Thr Gly Glu Leu
        290                 295                 300

Glu Leu Glu Glu Lys Lys Trp Arg Glu Ser Glu Thr Asn Ser Ile Glu
305                 310                 315                 320

Phe Trp Arg Pro Leu Phe Thr His Gln Pro Phe Leu Asp Ala Ile Gln
                325                 330                 335

Asp Lys Tyr Arg Ile Pro Asp Lys Glu Ile Thr Asp Gly Ala Ala Leu
            340                 345                 350

Glu Asp Leu Tyr Ser Thr Asp Glu Pro Glu Ser Asn Lys Ile Asp Leu
        355                 360                 365

Asp Asp Asp Ile Pro Asp Asp Ile Gly Ile Asp Gln Asp Glu Glu Pro
        370                 375                 380

Ile Met
385

<210> SEQ ID NO 16
<211> LENGTH: 335
<212> TYPE: PRT
<213> ORGANISM: Prochlorococcus phage P-SSM2

<400> SEQUENCE: 16

Met Asp Phe Leu Lys Glu Ile Val Lys Glu Ile Gly Asp Glu Tyr Thr
1               5                   10                  15

Gln Val Ala Ala Asp Ile Gln Glu Asn Glu Arg Phe Ile Asp Thr Gly
            20                  25                  30

Ser Tyr Ile Phe Asn Gly Leu Val Ser Gly Ser Ile Phe Gly Gly Val
        35                  40                  45

Ser Ser Ser Arg Ile Thr Ala Ile Ala Gly Glu Ser Thr Gly Lys
    50                  55                  60

Thr Tyr Phe Ser Leu Ala Val Val Lys Asn Phe Leu Asp Asn Asn Pro
65                  70                  75                  80

Asp Gly Tyr Cys Leu Tyr Phe Asp Thr Glu Ala Ala Val Asn Lys Gly
            85                  90                  95

Leu Leu Glu Ser Arg Gly Ile Asp Met Asn Arg Leu Val Val Val Asn
            100                 105                 110

Val Val Thr Ile Glu Glu Phe Arg Ser Lys Ala Leu Arg Ala Val Asp
        115                 120                 125

Ile Tyr Leu Lys Thr Ser Glu Glu Glu Arg Lys Pro Cys Met Phe Val
        130                 135                 140
```

```
Leu Asp Ser Leu Gly Met Leu Ser Thr Glu Lys Glu Ile Arg Asp Ala
145                 150                 155                 160

Leu Asp Asp Lys Gln Val Arg Asp Met Thr Lys Ser Gln Leu Val Lys
                165                 170                 175

Gly Ala Phe Arg Met Leu Thr Leu Lys Leu Gly Gln Ala Asn Ile Pro
            180                 185                 190

Leu Ile Val Thr Asn His Thr Tyr Asp Val Ile Gly Ser Tyr Val Pro
        195                 200                 205

Thr Lys Glu Met Gly Gly Ser Gly Leu Lys Tyr Ala Ala Ser Thr
210                 215                 220

Ile Ile Tyr Leu Ser Lys Lys Glu Lys Asp Gln Lys Glu Val Ile
225                 230                 235                 240

Gly Asn Leu Ile Lys Ala Lys Thr His Lys Ser Arg Leu Ser Lys Glu
                245                 250                 255

Asn Lys Glu Val Gln Ile Arg Leu Tyr Tyr Asp Glu Arg Gly Leu Asp
            260                 265                 270

Arg Tyr Tyr Gly Leu Leu Glu Leu Gly Glu Ile Gly Gly Met Trp Lys
        275                 280                 285

Asn Val Ala Gly Arg Tyr Glu Met Asn Gly Lys Lys Ile Tyr Ala Lys
290                 295                 300

Glu Ile Leu Lys Asn Pro Thr Glu Tyr Phe Thr Asp Asp Ile Met Glu
305                 310                 315                 320

Gln Leu Asp Asn Ile Ala Lys Glu His Phe Ser Tyr Gly Thr Asn
                325                 330                 335

<210> SEQ ID NO 17
<211> LENGTH: 336
<212> TYPE: PRT
<213> ORGANISM: Prochlorococcus phage P-SSM4

<400> SEQUENCE: 17

Met Asn Phe Leu Lys Asp Ile Ala Lys Glu Ile Gly Asn Asp Tyr Ala
1               5                   10                  15

Ser Leu Val Ser Glu Gly Val Ser Ala Gly Asp Thr Ala Gly Phe Ile
            20                  25                  30

Asp Thr Gly Ser Tyr Ile Phe Asn Ala Leu Leu Ser Gly Ser Ile Tyr
        35                  40                  45

Gly Gly Ile Pro Asn Asn Lys Ile Thr Ala Ile Ala Gly Glu Thr Ser
    50                  55                  60

Thr Gly Lys Thr Phe Phe Cys Leu Gly Met Val Gln His Phe Leu Glu
65                  70                  75                  80

Ser Asn Pro Asp Ala Gly Val Ile Tyr Phe Glu Ser Glu Ser Ala Ile
                85                  90                  95

Ser Lys Gln Met Ile Glu Asp Arg Gly Ile Asp Ser Asn Arg Met Leu
            100                 105                 110

Leu Val Pro Val Thr Thr Val Gln Glu Phe Arg Leu Gln Ala Ile Lys
        115                 120                 125

Ile Leu Asp Lys Tyr Asn Glu Gln Thr Ala Glu Glu Arg Lys Pro Leu
    130                 135                 140

Met Phe Val Leu Asp Ser Leu Gly Met Leu Ser Thr Ser Lys Glu Val
145                 150                 155                 160

Glu Asp Ser Glu Ala Gly Lys Glu Thr Arg Asp Met Thr Arg Ala Gln
                165                 170                 175

Val Val Lys Ser Ile Phe Arg Val Leu Thr Leu Lys Leu Gly Lys Ala
```

```
            180                 185                 190
Asn Val Pro Leu Ile Val Thr Asn His Thr Tyr Asp Val Val Gly Ala
            195                 200                 205
Tyr Ile Pro Thr Lys Glu Met Gly Gly Gly Ser Gly Leu Lys Tyr Ala
            210                 215                 220
Ala Ser Thr Ile Val Tyr Leu Ser Lys Lys Glu Lys Asn Gly Lys
225                 230                 235                 240
Glu Val Val Gly Asn Ile Ile Lys Cys Lys Thr Ala Lys Ser Arg Leu
                    245                 250                 255
Thr Lys Glu Asn Ser Asp Val Glu Thr Arg Leu Tyr Tyr Asp Arg Gly
                    260                 265                 270
Leu Asp Arg Tyr Tyr Gly Leu Leu Glu Leu Gly Glu Lys His Gly Val
                    275                 280                 285
Phe Ser Arg Lys Gly Asn Arg Val Val Val Gly Asp Ser Ser Val Tyr
                    290                 295                 300
Pro Ser Ala Ile Leu Ala Asp Pro Asp Lys Tyr Phe Thr Glu Glu Leu
305                 310                 315                 320
Met Glu Lys Leu Asp Glu Ala Ala Lys Glu Phe Arg Tyr Gly Asn
                    325                 330                 335

<210> SEQ ID NO 18
<211> LENGTH: 343
<212> TYPE: PRT
<213> ORGANISM: Synechococcus phage S-PM2

<400> SEQUENCE: 18

Met Ser Phe Leu Asp Ser Val Ile Lys Asp Ser Lys Asn Glu Tyr Ala
1               5                   10                  15
Ala Phe Ala Ser Glu Gly Val Ala Gly Asp Val Glu Ser Phe Val
                20                  25                  30
Asp Thr Gly Ser Tyr Ile Phe Asn Ala Leu Val Ser Gly Ser Ile Phe
            35                  40                  45
Gly Gly Ile Pro Ser Asn Lys Ile Thr Ala Leu Ala Gly Glu Ser Gly
        50                  55                  60
Thr Gly Lys Thr Phe Phe Cys Leu Ser Val Val Arg Asn Phe Leu Asn
65                  70                  75                  80
Thr Asp Pro Asp Ala Gly Val Ile Tyr Phe Glu Thr Glu Ser Ala Ile
                85                  90                  95
Ser Lys Gln Met Ile Glu Ser Arg Gly Ile Asp Ser Thr Arg Met Ile
                100                 105                 110
Ile Phe Pro Val Asp Thr Ile Glu Asp Phe Arg Thr Gln Ala Val Arg
            115                 120                 125
Ile Ile Asp Lys Tyr Met Glu Gln Asn Lys Ser Glu Arg Lys Pro Leu
        130                 135                 140
Met Phe Val Leu Asp Ser Leu Gly Met Leu Ala Thr Lys Lys Glu Val
145                 150                 155                 160
Glu Asp Ala Ser Asn Asp Lys Gln Val Arg Asp Met Thr Lys Ala Gln
                165                 170                 175
Ile Val Lys Ser Ala Phe Arg Ile Leu Thr Leu Lys Met Gly Lys Ala
                180                 185                 190
Asn Ile Pro Met Leu Val Thr Asn His Thr Tyr Asp Val Val Gly Ser
                195                 200                 205
Tyr Val Pro Thr Lys Glu Met Gly Gly Gly Ser Gly Leu Lys Tyr Ser
            210                 215                 220
```

```
Ala Ser Thr Ile Val Tyr Leu Gly Lys Lys Glu Lys Asp Gly Thr
225                 230                 235                 240

Asp Leu Val Gly Asn Ile Ile Lys Cys Glu Ala Lys Lys Ser Arg Leu
            245                 250                 255

Thr Arg Glu Gly Ser Lys Val Glu Thr Arg Leu Phe Phe Asp Gln Arg
            260                 265                 270

Gly Leu Glu Arg Tyr Tyr Gly Met Leu Glu Leu Gly Glu Arg Ala Gly
            275                 280                 285

Leu Trp Lys Asn Thr Ala Gly Arg Tyr Glu Ile Asn Gly Lys Lys Val
290                 295                 300

Tyr Gly Lys Gln Ile Leu Ala Asn Pro Asp Glu Phe Phe Thr Glu Glu
305                 310                 315                 320

Ile Leu Gln Glu Leu Asp Lys Gln Ala Gln Arg Glu Phe Leu Tyr Gly
                325                 330                 335

Ala Ser Asp Asp Gly Glu Asp
            340

<210> SEQ ID NO 19
<211> LENGTH: 393
<212> TYPE: PRT
<213> ORGANISM: Enterobacteria phage RB32

<400> SEQUENCE: 19

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys His Phe Lys Ser Asn Met Ser Leu Thr Met Val Ala Ala Tyr Leu
65                  70                  75                  80

Asn Lys Tyr Pro Asp Ala Val Cys Leu Phe Tyr Asp Ser Glu Phe Gly
                85                  90                  95

Ile Thr Pro Ala Tyr Leu Arg Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Ala Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255
```

```
Lys Phe Phe Ile Asp Val Lys Phe Asp Gly Ile Asp Pro Tyr Ser
            260                 265                 270

Gly Leu Leu Asp Met Ala Leu Glu Leu Gly Phe Val Lys Pro Lys
            275                 280                 285

Asn Gly Trp Tyr Ala Arg Glu Phe Leu Asp Glu Thr Gly Glu Met
            290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                    325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
            355                 360                 365

Glu Ser Lys Ser Lys Ser Ala Ala Asp Leu Thr Asp Leu Glu Gln
            370                 375                 380

Leu Ser Asp Met Glu Glu Phe Asn Glu
385                 390

<210> SEQ ID NO 20
<211> LENGTH: 366
<212> TYPE: PRT
<213> ORGANISM: Vibrio phage nt-1

<400> SEQUENCE: 20

Met Ser Asp Leu Leu Lys Ser Leu Lys Lys Ser Ser Thr Ser Gly Tyr
1               5                   10                  15

Ala His Val Leu Ser Glu Ser Gln Phe Met Phe Glu Lys Asp His Thr
            20                  25                  30

Arg Thr Tyr Val Pro Ala Ile Asn Ile Ala Phe Ser Gly Glu Val Asp
        35                  40                  45

Gly Gly Leu Thr Ser Gly Leu Thr Val Leu Ala Gly Pro Ser Lys His
    50                  55                  60

Phe Lys Ser Asn Leu Gly Leu Val Gly Val Ala Ala Tyr Leu Lys Lys
65                  70                  75                  80

Tyr Pro Glu Ala Ile Cys Val Phe Ile Asp Thr Glu Phe Gly Ile Thr
                85                  90                  95

Pro Ser Tyr Leu Lys Ser Gln Gly Val Asp Pro Glu Arg Val Leu His
            100                 105                 110

Ile Gln Cys Glu Ser Val Glu Arg Met Lys Phe Glu Met Ala Asn Gln
            115                 120                 125

Leu Lys Asp Leu Ala Glu Arg Lys Arg Ala Lys Lys Ala Gly Glu Glu
            130                 135                 140

Pro Asp Arg Val Val Phe Phe Ile Asp Ser Val Gly Asn Val Ala Ser
145                 150                 155                 160

Ala Lys Glu Ile Asp Asp Ala Gln Asn Glu Lys Ser Val Ala Asp Met
                165                 170                 175

Ser Arg Ala Lys Gln Leu Lys Ser Leu Phe Arg Ile Ile Thr Pro Tyr
            180                 185                 190

Phe Thr Met Leu Asp Ile Pro Cys Ile Ala Ile Asn His Thr Tyr Gln
            195                 200                 205

Thr Gln Glu Met Tyr Ser Lys Thr Val Met Ser Gly Thr Gly Ile
            210                 215                 220

Met Tyr Ser Ala Asp Thr Val Ile Ile Leu Gly Lys Gln Gln Glu Lys
```

```
            225                 230                 235                 240

Asp Gly Lys Glu Ile Ile Gly Tyr His Phe Ile Met Asn Ile Glu Lys
                245                 250                 255

Ser Arg Phe Val Lys Glu Lys Met Lys Val Pro Leu Thr Val Thr Tyr
                260                 265                 270

Glu His Gly Ile Asp Gln Phe Ser Gly Leu Leu Asp Ile Ala Leu Gln
                275                 280                 285

Thr Gly His Val Lys Pro Ser Asn Gly Trp Tyr Gln Arg Ala Phe
                290                 295                 300

Ile Asp Glu Glu Thr Gly Glu Ile Glu Ile Glu Lys Lys Tyr Arg
305                 310                 315                 320

Ala Lys Glu Thr Gln Thr Leu Ser Phe Trp Lys Ile Ile Asn Ser
                325                 330                 335

Pro Thr Phe Lys Thr Gly Val Lys Arg Leu Tyr Cys Leu Gly Gln Leu
                340                 345                 350

Asp Glu Ser Glu Leu Leu Asp Glu Val Asp Ser Leu Phe Asp
                355                 360                 365
```

<210> SEQ ID NO 21
<211> LENGTH: 381
<212> TYPE: PRT
<213> ORGANISM: Enterobacteria phage RB16

<400> SEQUENCE: 21

```
Met Ser Asn Lys Ala Leu Leu Lys Lys Leu Ile Lys Asn Ser Asn Ser
1               5                   10                  15

Gln Ser Ala Ser Ile Leu Ser Glu Ser Asp Val Phe Asn Asn Ile Thr
                20                  25                  30

Lys Thr Arg Thr Arg Val Pro Ile Leu Asn Leu Val Leu Ser Gly Ala
                35                  40                  45

Phe Asp Gly Gly Leu Thr Ser Gly Leu Thr Leu Ile Ala Gly Pro Ser
            50                  55                  60

Lys His Phe Lys Ser Asn Leu Gly Leu Val Ala Val Ala Ala Tyr Leu
65              70                  75                  80

Lys Ala Asn Glu Asp Ala Val Cys Leu Phe Tyr Asp Ser Glu Lys Gly
                85                  90                  95

Val Thr Lys Ser Tyr Leu Lys Ser Met Gly Val Asp Pro Asp Arg Val
                100                 105                 110

Val Tyr Thr Arg Ile Thr Thr Val Glu Gln Leu Arg Asn Asp Val Val
                115                 120                 125

Ser Gln Leu Asp Ala Leu Glu Arg Gly Asp Lys Val Ile Ile Phe Val
            130                 135                 140

Asp Ser Val Gly Asn Thr Ala Ser Lys Lys Glu Leu Lys Asp Ala Leu
145                 150                 155                 160

Glu Asp Asn Asp Lys Gln Asp Met Thr Arg Ala Lys Ala Leu Lys Gly
                165                 170                 175

Met Phe Arg Met Val Thr Pro Tyr Leu Ala Asp Ile Asp Ile Pro Met
                180                 185                 190

Val Cys Ile Cys His Thr Tyr Asp Thr Gln Glu Met Tyr Ser Lys Lys
                195                 200                 205

Val Ile Ser Gly Gly Thr Gly Leu Met Tyr Ser Ala Asp Thr Ala Ile
            210                 215                 220

Ile Leu Gly Lys Gln Gln Val Leu Glu Gly Thr Glu Val Val Gly Tyr
225                 230                 235                 240
```

```
Asp Phe Ile Met Asn Val Glu Lys Ser Arg Phe Val Lys Glu Lys Ser
                245                 250                 255

Lys Phe Pro Leu His Val Thr Tyr Glu Gly Gly Ile Ser Met Phe Ser
            260                 265                 270

Gly Leu Leu Asp Leu Ala Met Glu Met Asn Phe Val Gln Thr Pro Thr
        275                 280                 285

Lys Gly Trp Arg Gly Arg Ala Phe Leu Asn Thr Glu Thr Gly Glu Leu
    290                 295                 300

Glu Leu Glu Glu Lys Lys Trp Arg Glu Ala Glu Thr Asn Cys Ile Glu
305                 310                 315                 320

Phe Trp Lys Pro Leu Phe Lys His Gln Pro Phe Ile Asp Ala Ile Gln
                325                 330                 335

Asp Lys Tyr Arg Ile Pro Asp Lys Glu Ile Thr Asp Gly Ala Ala Leu
            340                 345                 350

Glu Asp Leu Tyr Ser Asp Asp Val Glu Ser Asn Lys Val Asp Phe
        355                 360                 365

Asp Asp Asp Ile Pro Asp Asp Val Asp Leu Met Glu Glu
    370                 375                 380

<210> SEQ ID NO 22
<211> LENGTH: 391
<212> TYPE: PRT
<213> ORGANISM: Enterobacteria phage T4

<400> SEQUENCE: 22

Met Ser Asp Leu Lys Ser Arg Leu Ile Lys Ala Ser Thr Ser Lys Leu
1               5                   10                  15

Thr Ala Glu Leu Thr Ala Ser Lys Phe Phe Asn Glu Lys Asp Val Val
                20                  25                  30

Arg Thr Lys Ile Pro Met Met Asn Ile Ala Leu Ser Gly Glu Ile Thr
            35                  40                  45

Gly Gly Met Gln Ser Gly Leu Leu Ile Leu Ala Gly Pro Ser Lys Ser
        50                  55                  60

Phe Lys Ser Asn Phe Gly Leu Thr Met Val Ser Ser Tyr Met Arg Gln
65              70                  75                  80

Tyr Pro Asp Ala Val Cys Leu Phe Tyr Asp Ser Glu Phe Gly Ile Thr
                85                  90                  95

Pro Ala Tyr Leu Arg Ser Met Gly Val Asp Pro Glu Arg Val Ile His
            100                 105                 110

Thr Pro Val Gln Ser Leu Glu Gln Leu Arg Ile Asp Met Val Asn Gln
        115                 120                 125

Leu Asp Ala Ile Glu Arg Gly Glu Lys Val Val Val Phe Ile Asp Ser
    130                 135                 140

Leu Gly Asn Leu Ala Ser Lys Lys Glu Thr Glu Asp Ala Leu Asn Glu
145                 150                 155                 160

Lys Val Val Ser Asp Met Thr Arg Ala Lys Thr Met Lys Ser Leu Phe
                165                 170                 175

Arg Ile Val Thr Pro Tyr Phe Ser Thr Lys Asn Ile Pro Cys Ile Ala
            180                 185                 190

Ile Asn His Thr Tyr Glu Thr Gln Glu Met Phe Ser Lys Thr Val Met
        195                 200                 205

Gly Gly Gly Thr Gly Pro Met Tyr Ser Ala Asp Thr Val Phe Ile Ile
    210                 215                 220

Gly Lys Arg Gln Ile Lys Asp Gly Ser Asp Leu Gln Gly Tyr Gln Phe
225                 230                 235                 240
```

```
Val Leu Asn Val Glu Lys Ser Arg Thr Val Lys Glu Lys Ser Lys Phe
                245                 250                 255

Lys Ile Asp Val Lys Phe Asp Gly Gly Ile Asp Pro Tyr Ser Gly Leu
            260                 265                 270

Leu Asp Met Ala Leu Glu Leu Gly Phe Val Val Lys Pro Lys Asn Gly
        275                 280                 285

Trp Tyr Ala Arg Glu Phe Leu Asp Glu Glu Thr Gly Glu Met Ile Arg
    290                 295                 300

Glu Glu Lys Ser Trp Arg Ala Lys Asp Thr Asn Cys Thr Thr Phe Trp
305                 310                 315                 320

Gly Pro Leu Phe Lys His Gln Pro Phe Arg Asp Ala Ile Lys Arg Ala
                325                 330                 335

Tyr Gln Leu Gly Ala Ile Asp Ser Asn Glu Ile Val Glu Ala Glu Val
            340                 345                 350

Asp Glu Leu Ile Asn Ser Lys Val Glu Lys Phe Lys Ser Pro Glu Ser
        355                 360                 365

Lys Ser Lys Ser Ala Ala Asp Leu Glu Thr Asp Leu Glu Gln Leu Ser
    370                 375                 380

Asp Met Glu Glu Phe Asn Glu
385                 390

<210> SEQ ID NO 23
<211> LENGTH: 393
<212> TYPE: PRT
<213> ORGANISM: Enterobacteria phage T6

<400> SEQUENCE: 23

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
                20                  25                  30

Val Ile Arg Thr Lys Ile Pro Met Leu Asn Ile Ala Ile Ser Gly Ala
            35                  40                  45

Ile Asp Gly Gly Met Gln Ser Gly Leu Thr Ile Phe Ala Gly Pro Ser
        50                  55                  60

Lys His Phe Lys Ser Asn Met Ser Leu Thr Met Val Ala Ala Tyr Leu
65                  70                  75                  80

Asn Lys Tyr Pro Asp Ala Val Cys Leu Phe Tyr Asp Ser Glu Phe Gly
                85                  90                  95

Ile Thr Pro Ala Tyr Leu Arg Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Ala Ile Glu Arg Gly Glu Lys Val Ile Val Phe Ile
130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
```

```
                210                 215                 220
Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Lys Ile Asp Val Lys Phe Asp Gly Gly Ile Asp Pro Tyr Ser
                260                 265                 270

Gly Leu Leu Asp Met Ala Leu Glu Leu Gly Phe Val Val Lys Pro Lys
                275                 280                 285

Asn Gly Trp Tyr Ala Arg Glu Phe Leu Asp Glu Glu Thr Gly Glu Met
                290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
                340                 345                 350

Glu Val Asp Glu Leu Ile Asn Ser Lys Val Glu Lys Phe Lys Ser Pro
                355                 360                 365

Glu Ser Lys Ser Lys Ser Ala Ala Asp Leu Glu Thr Asp Leu Glu Gln
370                 375                 380

Leu Ser Asp Met Glu Glu Phe Asn Glu
385                 390

<210> SEQ ID NO 24
<211> LENGTH: 387
<212> TYPE: PRT
<213> ORGANISM: Acinetobacter phage 133

<400> SEQUENCE: 24

Met Ser Ser Leu Lys Glu Arg Leu Ile Lys Ala Ser Thr Ser Lys Met
1               5                   10                  15

Thr Ala Glu Leu Thr Lys Ser Lys Phe Phe Asn Asp Lys Thr Val Val
                20                  25                  30

Arg Thr Arg Ile Pro Met Leu Asn Ile Ala Ile Ser Gly Ala Leu Asn
                35                  40                  45

Gly Gly Met Gln Ser Gly Leu Thr Ile Phe Ala Gly Pro Ser Lys His
50                  55                  60

Phe Lys Ser Asn Met Gly Leu Thr Met Val Ala Ala Tyr Met Lys Ala
65                  70                  75                  80

Phe Pro Asp Ala Val Cys Met Phe Tyr Asp Ser Glu Phe Gly Ile Thr
                85                  90                  95

Pro Ala Tyr Leu Lys Ala Met Gly Val Asp Pro Asp Arg Val Ile His
                100                 105                 110

Thr Pro Val Gln Ser Val Glu Gln Leu Lys Ile Asp Met Thr Asn Gln
                115                 120                 125

Leu Glu Glu Val Lys Arg Gly Glu Lys Val Ile Val Phe Ile Asp Ser
                130                 135                 140

Ile Gly Asn Leu Ala Ser Lys Lys Glu Thr Glu Asp Ala Leu Asn Glu
145                 150                 155                 160

Lys Thr Thr Ala Asp Met Thr Arg Ala Lys Ala Leu Lys Ser Leu Phe
                165                 170                 175

Arg Ile Val Thr Pro Tyr Phe Ser Ile Lys Asp Ile Pro Cys Val Ala
                180                 185                 190
```

Val Asn His Thr Leu Gln Thr Leu Glu Met Phe Ser Lys Glu Val Met
195                 200                 205

Thr Gly Gly Thr Gly Val Met Tyr Ser Ala Asp Thr Val Phe Phe Ile
210                 215                 220

Gly Lys Arg Gln Val Lys Asp Gly Thr Glu Leu Ala Gly Tyr Glu Phe
225                 230                 235                 240

Ile Leu Lys Ala Glu Lys Ser Arg Met Val Lys Glu Lys Ser Val Phe
                245                 250                 255

Lys Ile Thr Val Lys Phe Asp Gly Gly Ile Asp Pro Tyr Ser Gly Leu
            260                 265                 270

Leu Glu Met Ala Thr Asp Leu Gly Phe Val Val Lys Pro Lys Val Gly
        275                 280                 285

Trp Tyr Lys Arg Ala Met Met Val Asp Gly Val Met Gln His Glu Glu
290                 295                 300

Lys Ser Trp Arg Ala Lys Asp Thr Asp Ser Ile Asp Phe Trp Gly Pro
305                 310                 315                 320

Leu Phe Lys His Asp Glu Phe Arg Lys Ala Ile Glu Thr Arg Tyr Gln
                325                 330                 335

Leu Gly Ser Ile Glu Ser Asp Ala Glu Val Asp Ala Glu Val Asp Ala
            340                 345                 350

Leu Ile Gly Ser Lys Thr Thr Ala Lys Ile Ser Gly Val Asn Phe Gly
        355                 360                 365

Pro Ala Glu Ser Ala Ala Asp Lys Glu Gln Gln Leu Glu Asp Phe Val
370                 375                 380

Asp Glu Asp
385

<210> SEQ ID NO 25
<211> LENGTH: 390
<212> TYPE: PRT
<213> ORGANISM: Enterobacteria phage RB69

<400> SEQUENCE: 25

Met Ser Asp Leu Lys Ser Arg Leu Ile Lys Ala Ser Thr Ser Lys Met
1               5                   10                  15

Thr Ala Asp Leu Thr Lys Ser Lys Leu Phe Asn Asn Arg Asp Glu Val
            20                  25                  30

Pro Thr Arg Ile Pro Met Leu Asn Ile Ala Leu Gly Gly Ala Leu Asn
        35                  40                  45

Ala Gly Leu Gln Ser Gly Leu Thr Ile Phe Ala Ala Pro Ser Lys His
50                  55                  60

Phe Lys Thr Leu Phe Gly Leu Thr Met Val Ala Ala Tyr Met Lys Lys
65                  70                  75                  80

Tyr Lys Asp Ala Ile Cys Leu Phe Tyr Asp Ser Glu Phe Gly Ala Ser
                85                  90                  95

Glu Ser Tyr Phe Arg Ser Met Gly Val Asp Leu Asp Arg Val Val His
            100                 105                 110

Thr Pro Ile Gln Ser Val Glu Gln Leu Lys Val Asp Met Thr Asn Gln
        115                 120                 125

Leu Asp Ala Ile Glu Arg Gly Asp Lys Val Ile Phe Ile Asp Ser
130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

```
Arg Ile Val Thr Pro Tyr Leu Thr Ile Lys Asp Ile Pro Cys Val Ala
            180                 185                 190

Ile Asn His Thr Ala Met Glu Ile Gly Gly Leu Tyr Pro Lys Glu Ile
        195                 200                 205

Met Gly Gly Gly Thr Gly Ile Leu Tyr Ser Ala Asn Thr Val Phe Phe
210                 215                 220

Ile Ser Lys Arg Gln Val Lys Glu Gly Thr Glu Leu Thr Gly Tyr Asp
225                 230                 235                 240

Phe Thr Leu Lys Ala Glu Lys Ser Arg Thr Val Lys Glu Lys Ser Thr
                245                 250                 255

Phe Lys Ile Thr Val Asn Phe Asp Gly Gly Ile Asp Pro Phe Ser Gly
            260                 265                 270

Leu Leu Glu Met Ala Thr Glu Ile Gly Phe Val Val Lys Pro Lys Ala
        275                 280                 285

Gly Trp Tyr Ala Arg Glu Phe Leu Asp Glu Thr Gly Glu Met Ile
290                 295                 300

Arg Glu Glu Lys Ser Trp Arg Ala Lys Ala Thr Asp Cys Val Glu Phe
305                 310                 315                 320

Trp Gly Pro Leu Phe Lys His Lys Pro Phe Arg Asp Ala Ile Glu Thr
                325                 330                 335

Lys Tyr Lys Leu Gly Ala Ile Ser Ser Ile Lys Glu Val Asp Asp Ala
            340                 345                 350

Val Asn Asp Leu Ile Asn Cys Lys Ala Thr Thr Lys Val Pro Val Lys
        355                 360                 365

Thr Ser Asp Ala Pro Ser Ala Ala Asp Ile Glu Asn Asp Leu Asp Glu
370                 375                 380

Met Glu Asp Phe Asp Glu
385                 390

<210> SEQ ID NO 26
<211> LENGTH: 411
<212> TYPE: PRT
<213> ORGANISM: Aeromonas phage Aeh1

<400> SEQUENCE: 26

Met Ala Lys Gly Ile Lys Thr Ala Lys Thr Gly Asn Leu Gly Ser Leu
1               5                   10                  15

Met Ser Lys Leu Ala Gly Thr Ser Ser Asn Lys Met Ser Ser Val Leu
            20                  25                  30

Ala Asp Ser Lys Phe Phe Asn Asp Lys Asp Cys Val Arg Thr Arg Val
        35                  40                  45

Pro Leu Leu Asn Leu Ala Met Ser Gly Glu Leu Asp Gly Gly Leu Thr
50                  55                  60

Pro Gly Leu Thr Val Leu Ala Gly Pro Ser Lys His Phe Lys Ser Asn
65                  70                  75                  80

Leu Ser Leu Val Phe Val Ala Ala Tyr Leu Arg Lys Tyr Pro Asp Ala
                85                  90                  95

Val Cys Ile Phe Phe Asp Asn Glu Phe Gly Ser Thr Pro Gly Tyr Phe
            100                 105                 110

Glu Ser Gln Gly Val Asp Ile Ser Arg Val Ile His Cys Pro Phe Lys
        115                 120                 125

Asn Ile Glu Glu Leu Lys Phe Asp Ile Val Lys Lys Leu Glu Ala Ile
130                 135                 140

Glu Arg Gly Asp Arg Val Ile Val Phe Val Asp Ser Ile Gly Asn Ala
```

| | | | | 145 | | | | | 150 | | | | | 155 | | | | | 160 |

Ala Ser Lys Lys Glu Ile Asp Asp Ala Ile Asp Glu Lys Ser Val Ser
             165                 170                 175

Asp Met Thr Arg Ala Lys Gln Ile Lys Ser Leu Thr Arg Met Met Thr
             180                 185                 190

Pro Tyr Leu Thr Val Asn Asp Ile Pro Ala Ile Met Val Ala His Thr
             195                 200                 205

Tyr Asp Thr Gln Glu Met Tyr Ser Lys Val Val Ser Gly Gly Thr
    210                 215                 220

Gly Ile Thr Tyr Ser Ser Asp Thr Val Ile Ile Gly Arg Gln Gln
225                 230                 235                 240

Glu Lys Asp Gly Lys Glu Leu Leu Gly Tyr Asn Phe Val Leu Asn Met
             245                 250                 255

Glu Lys Ser Arg Phe Val Lys Glu Gln Ser Lys Leu Lys Leu Glu Val
             260                 265                 270

Thr Phe Gln Gly Gly Ile Asn Thr Tyr Ser Gly Met Leu Asp Ile Ala
             275                 280                 285

Leu Glu Val Gly Phe Val Val Lys Pro Ser Asn Gly Trp Phe Ser Arg
    290                 295                 300

Ala Phe Leu Asp Glu Glu Thr Gly Glu Leu Val Glu Asp Arg Lys
305                 310                 315                 320

Trp Arg Arg Ala Asp Thr Asn Cys Leu Glu Phe Trp Lys Pro Met Phe
             325                 330                 335

Ala His Gln Pro Phe Lys Thr Ala Cys Ser Asp Met Phe Lys Leu Lys
             340                 345                 350

Ser Val Ala Val Lys Asp Glu Val Phe Asp Glu Val Asp Glu Leu Phe
             355                 360                 365

Ser Gly Glu Ala Glu Met Pro Val Asn Met Gly Arg Lys Leu Asp Thr
    370                 375                 380

Ala Asp Gln Glu Glu Ile Asp Gln Leu Glu Glu Val Asp Val Glu Gly
385                 390                 395                 400

Ser Asp Ser Asp Glu Leu Phe Ala Asn Leu Asp
             405                 410

<210> SEQ ID NO 27
<211> LENGTH: 368
<212> TYPE: PRT
<213> ORGANISM: Aeromonas phage 65

<400> SEQUENCE: 27

Met Ala Lys Lys Ala Lys Val Val Asn Ser Gly Asp Leu Leu Glu Arg
1               5                   10                  15

Leu Asn Gly Thr Ser Ser Asn Lys Met Ser Ala Met Leu Ala Glu Ser
             20                  25                  30

Ile Phe Phe Asn Glu Lys Asp Thr Ile Arg Thr Arg Val Pro Ile Ile
             35                  40                  45

Asn Leu Met Met Ser Gly Arg Leu Asp Gly Gly Ile Thr Pro Gly Leu
    50                  55                  60

Thr Cys Ile Ala Gly Pro Ser Lys His Phe Lys Ser Asn Leu Ser Leu
65                  70                  75                  80

Val Met Val Ser Ala Tyr Leu Arg Lys Tyr Pro Lys Ala Val Cys Leu
             85                  90                  95

Phe Phe Asp Asn Glu Phe Gly Ser Thr Pro Asp Tyr Phe Thr Ser Gln
             100                 105                 110

```
Gly Val Asp Ile Ser Arg Val His Cys Pro Phe Ile Asp Val Glu
            115                 120                 125

Glu Leu Lys Phe Asp Ile Val Lys Lys Leu Glu Ser Ile Thr Arg Gly
130                 135                 140

Asp Lys Val Ile Ile Tyr Ile Asp Ser Ile Gly Asn Val Ala Ser Lys
145                 150                 155                 160

Lys Glu Leu Gln Asp Ala Lys Asp Glu Lys Ser Ala Gln Asp Met Thr
            165                 170                 175

Arg Ala Lys Gln Ile Lys Ser Leu Phe Arg Met Val Thr Pro Tyr Leu
            180                 185                 190

Thr Val Leu Asp Ile Pro Cys Ile Ala Val Asn His Thr Tyr Glu Thr
            195                 200                 205

Gln Glu Met Phe Ser Lys Thr Val Met Ser Gly Gly Thr Gly Pro Met
210                 215                 220

Tyr Ser Ala Asp Thr Val Ile Ile Leu Gly Lys Gln Gln Asp Lys Asp
225                 230                 235                 240

Gly Lys Glu Leu Leu Gly Tyr Asn Phe Val Met Asn Ala Glu Lys Ser
            245                 250                 255

Arg Ala Ile Lys Glu Lys Ser Lys Leu Lys Leu Met Val Ser Phe Glu
            260                 265                 270

Gly Gly Ile Asn Thr Tyr Ser Gly Leu Leu Lys Ile Ala Gln Glu Leu
            275                 280                 285

Gly Phe Val Thr Lys Pro Gln Asn Ala Arg Tyr Gln Arg Asn Phe Leu
            290                 295                 300

Asp Leu Glu Pro Gly Glu Met Val Ile Pro Glu Asp Glu Lys Lys Trp
305                 310                 315                 320

Thr Glu Glu Glu Ser Asp Ser Leu Glu Phe Trp Lys Pro Met Phe Ser
            325                 330                 335

His Lys Pro Phe Met Asp Ala Val Ser Asn Ala Tyr Lys Leu Lys Ala
            340                 345                 350

Val Glu Val Ser Gln Glu Val Phe Asp Glu Val Asp Gln Leu Phe Gly
            355                 360                 365

<210> SEQ ID NO 28
<211> LENGTH: 366
<212> TYPE: PRT
<213> ORGANISM: Vibrio phage KVP40

<400> SEQUENCE: 28

Met Ser Asp Leu Met Lys Ser Leu Lys Lys Ser Ser Thr Ser Gly Tyr
1               5                   10                  15

Ala Gln Val Leu Ser Glu Ser Gln Phe Met Phe Asp Lys Asp His Thr
            20                  25                  30

Arg Thr Tyr Val Pro Ala Ile Asn Ile Ala Phe Ser Gly Glu Val Asp
            35                  40                  45

Gly Gly Leu Thr Ser Gly Leu Thr Val Leu Ala Gly Pro Ser Lys His
        50                  55                  60

Phe Lys Ser Asn Leu Gly Leu Val Gly Val Ala Ala Tyr Leu Lys Lys
65                  70                  75                  80

Tyr Pro Asp Ala Val Cys Val Phe Ile Asp Thr Glu Phe Gly Ile Thr
            85                  90                  95

Pro Ser Tyr Leu Arg Ser Gln Gly Val Asp Pro Asp Arg Val Leu His
            100                 105                 110

Ile Gln Cys Glu Ser Val Glu Arg Met Lys Phe Glu Met Ala Asn Gln
            115                 120                 125
```

Leu Lys Asp Leu Ala Glu Arg Lys Ala Lys Ala Gly Glu Glu
    130                 135                 140

Pro Asp Arg Val Ile Phe Phe Ile Asp Ser Val Gly Asn Val Ala Ser
145                 150                 155                 160

Ala Lys Glu Ile Asp Asp Ala Gln Asn Glu Lys Ser Val Ala Asp Met
                165                 170                 175

Ser Arg Ala Lys Gln Leu Lys Ser Leu Phe Arg Ile Ile Thr Pro Tyr
            180                 185                 190

Phe Thr Met Leu Asp Ile Pro Cys Ile Ala Ile Asn His Thr Tyr Gln
        195                 200                 205

Thr Gln Glu Ile Tyr Ser Lys Thr Val Met Ser Gly Thr Gly Ile
    210                 215                 220

Met Tyr Ser Ala Asp Thr Val Ile Ile Leu Gly Lys Gln Gln Glu Lys
225                 230                 235                 240

Asp Gly Lys Asp Ile Ile Gly Tyr His Phe Ile Met Asn Ile Glu Lys
                245                 250                 255

Ser Arg Phe Val Lys Glu Lys Met Lys Val Lys Leu Thr Val Thr Tyr
            260                 265                 270

Glu Asn Gly Ile Asp Pro Phe Ser Gly Leu Leu Asp Ile Ala Leu Gln
        275                 280                 285

Thr Gly His Val Val Lys Pro Ser Asn Gly Trp Tyr Gln Arg Ala Thr
    290                 295                 300

Val Asp Glu Glu Thr Gly Glu Met Ile Val Glu Glu Lys Lys Tyr Arg
305                 310                 315                 320

Ala Lys Glu Thr Gln Thr Ile Ser Phe Trp Lys Asp Ile Ile Asn Ser
                325                 330                 335

Pro Thr Phe Lys Glu Gly Val Lys Arg Ile Tyr Cys Leu Gly Gln Leu
            340                 345                 350

Asp Glu Ser Glu Leu Phe Gly Glu Val Asp Ser Leu Phe Asp
        355                 360                 365

<210> SEQ ID NO 29
<211> LENGTH: 386
<212> TYPE: PRT
<213> ORGANISM: Enterobacteria phage RB43

<400> SEQUENCE: 29

Met Ser Asn Lys Ala Leu Leu Lys Lys Leu Ile Lys Asn Ser Asn Ser
1               5                   10                  15

Gln Ser Ala Ala Ile Leu Ser Glu Ser Asp Val Phe Asn Asn Ile Thr
            20                  25                  30

Lys Thr Arg Thr Arg Val Pro Ile Leu Asn Leu Ala Leu Ser Gly Ala
        35                  40                  45

Phe Asp Gly Gly Leu Thr Ser Gly Leu Thr Leu Phe Ala Gly Pro Ser
    50                  55                  60

Lys His Phe Lys Ser Asn Leu Gly Leu Val Thr Val Ser Ala Tyr Leu
65                  70                  75                  80

Lys Ala Asn Glu Asp Ala Val Cys Leu Phe Tyr Asp Ser Glu Lys Gly
                85                  90                  95

Val Thr Lys Ser Tyr Leu Lys Ser Met Gly Val Asp Pro Asp Arg Val
            100                 105                 110

Val Tyr Thr Arg Ile Thr Thr Val Glu Gln Leu Arg Asn Asp Val Val
        115                 120                 125

Ser Gln Leu Asp Ala Leu Glu Arg Gly Asp Lys Val Ile Ile Phe Val

```
            130                 135                 140
Asp Ser Val Gly Asn Thr Ala Ser Lys Lys Glu Leu Ala Asp Ala Leu
145                 150                 155                 160

Ser Asp Asn Asp Lys Gln Asp Met Thr Arg Ala Lys Ala Leu Lys Gly
                165                 170                 175

Met Phe Arg Met Val Thr Pro Tyr Leu Ala Asp Leu Asp Ile Pro Met
            180                 185                 190

Val Cys Ile Cys His Thr Tyr Asp Thr Gln Glu Met Tyr Ser Lys Lys
        195                 200                 205

Val Ile Ser Gly Gly Thr Gly Leu Met Tyr Ser Ala Asp Thr Ala Ile
    210                 215                 220

Ile Leu Gly Lys Gln Gln Val Lys Glu Gly Thr Glu Val Val Gly Tyr
225                 230                 235                 240

Asp Phe Ile Met Asn Ile Glu Lys Ser Arg Phe Val Lys Glu Lys Ser
                245                 250                 255

Lys Phe Lys Leu His Val Thr Tyr Glu Gly Gly Ile Ser Met Tyr Ser
            260                 265                 270

Gly Leu Leu Asp Leu Ala Met Glu Met Asn Phe Val Gln Thr Pro Thr
        275                 280                 285

Lys Gly Trp Arg Gly Arg Ala Phe Leu Asn Thr Glu Thr Gly Glu Leu
    290                 295                 300

Glu Leu Glu Glu Lys Lys Trp Arg Glu Ser Thr Asn Ser Ile Glu
305                 310                 315                 320

Phe Trp Arg Pro Leu Phe Thr His Gln Pro Phe Leu Asp Ala Ile Gln
                325                 330                 335

Asp Lys Tyr Arg Ile Pro Asp Lys Glu Ile Thr Asp Gly Ala Ala Leu
            340                 345                 350

Glu Asp Leu Tyr Ser Thr Asp Glu Pro Glu Ser Asn Lys Ile Asp Leu
        355                 360                 365

Asp Asp Asp Ile Pro Asp Ile Gly Ile Asp Gln Asp Glu Pro
    370                 375                 380

Ile Met
385

<210> SEQ ID NO 30
<211> LENGTH: 335
<212> TYPE: PRT
<213> ORGANISM: Prochlorococcus phage P-SSM2

<400> SEQUENCE: 30

Met Asp Phe Leu Lys Glu Ile Val Lys Glu Ile Gly Asp Glu Tyr Thr
1               5                   10                  15

Gln Val Ala Ala Asp Ile Gln Glu Asn Glu Arg Phe Ile Asp Thr Gly
            20                  25                  30

Ser Tyr Ile Phe Asn Gly Leu Val Ser Gly Ser Ile Phe Gly Gly Val
        35                  40                  45

Ser Ser Ser Arg Ile Thr Ala Ile Ala Gly Glu Ser Ser Thr Gly Lys
    50                  55                  60

Thr Tyr Phe Ser Leu Ala Val Val Lys Asn Phe Leu Asp Asn Asn Pro
65                  70                  75                  80

Asp Gly Tyr Cys Leu Tyr Phe Asp Thr Glu Ala Ala Val Asn Lys Gly
                85                  90                  95

Leu Leu Glu Ser Arg Gly Ile Asp Met Asn Arg Leu Val Val Val Asn
            100                 105                 110
```

Val Val Thr Ile Glu Glu Phe Arg Ser Lys Ala Leu Arg Ala Val Asp
            115                 120                 125

Ile Tyr Leu Lys Thr Ser Glu Glu Arg Lys Pro Cys Met Phe Val
130                 135                 140

Leu Asp Ser Leu Gly Met Leu Ser Thr Glu Lys Glu Ile Arg Asp Ala
145                 150                 155                 160

Leu Asp Asp Lys Gln Val Arg Asp Met Thr Lys Ser Gln Leu Val Lys
                165                 170                 175

Gly Ala Phe Arg Met Leu Thr Leu Lys Leu Gly Gln Ala Asn Ile Pro
            180                 185                 190

Leu Ile Val Thr Asn His Thr Tyr Asp Val Ile Gly Ser Tyr Val Pro
            195                 200                 205

Thr Lys Glu Met Gly Gly Gly Ser Gly Leu Lys Tyr Ala Ala Ser Thr
210                 215                 220

Ile Ile Tyr Leu Ser Lys Lys Glu Lys Asp Gln Lys Glu Val Ile
225                 230                 235                 240

Gly Asn Leu Ile Lys Ala Lys Thr His Lys Ser Arg Leu Ser Lys Glu
            245                 250                 255

Asn Lys Glu Val Lys Ile Arg Leu Tyr Tyr Asp Glu Arg Gly Leu Asp
            260                 265                 270

Arg Tyr Tyr Gly Leu Leu Glu Leu Gly Glu Ile Gly Gly Met Trp Lys
        275                 280                 285

Asn Val Ala Gly Arg Tyr Glu Met Asn Gly Lys Lys Ile Tyr Ala Lys
            290                 295                 300

Glu Ile Leu Lys Asn Pro Thr Glu Tyr Phe Thr Asp Asp Ile Met Glu
305                 310                 315                 320

Gln Leu Asp Asn Ile Ala Lys Glu His Phe Ser Tyr Gly Thr Asn
                325                 330                 335

<210> SEQ ID NO 31
<211> LENGTH: 336
<212> TYPE: PRT
<213> ORGANISM: Prochlorococcus phage P-SSM4

<400> SEQUENCE: 31

Met Asn Phe Leu Lys Asp Ile Ala Lys Glu Ile Gly Asn Asp Tyr Ala
1               5                   10                  15

Ser Leu Val Ser Glu Gly Val Ser Ala Gly Asp Thr Ala Gly Phe Ile
            20                  25                  30

Asp Thr Gly Ser Tyr Ile Phe Asn Ala Leu Leu Ser Gly Ser Ile Tyr
        35                  40                  45

Gly Gly Ile Pro Asn Asn Lys Ile Thr Ala Ile Ala Gly Glu Thr Ser
    50                  55                  60

Thr Gly Lys Thr Phe Phe Cys Leu Gly Met Val Gln His Phe Leu Glu
65                  70                  75                  80

Ser Asn Pro Asp Ala Gly Val Ile Tyr Phe Glu Ser Glu Ser Ala Ile
                85                  90                  95

Ser Lys Gln Met Ile Glu Asp Arg Gly Ile Asp Ser Asn Arg Met Leu
            100                 105                 110

Leu Val Pro Val Thr Thr Val Gln Glu Phe Arg Leu Gln Ala Ile Lys
        115                 120                 125

Ile Leu Asp Lys Tyr Asn Glu Gln Thr Ala Glu Glu Arg Lys Pro Leu
    130                 135                 140

Met Phe Val Leu Asp Ser Leu Gly Met Leu Ser Thr Ser Lys Glu Val
145                 150                 155                 160

Glu Asp Ser Glu Ala Gly Lys Glu Thr Arg Asp Met Thr Arg Ala Gln
                165                 170                 175

Val Val Lys Ser Ile Phe Arg Val Leu Thr Leu Lys Leu Gly Lys Ala
            180                 185                 190

Asn Val Pro Leu Ile Val Thr Asn His Thr Tyr Asp Val Val Gly Ala
        195                 200                 205

Tyr Ile Pro Thr Lys Glu Met Gly Gly Gly Ser Gly Leu Lys Tyr Ala
    210                 215                 220

Ala Ser Thr Ile Val Tyr Leu Ser Lys Lys Glu Lys Asn Gly Lys
225                 230                 235                 240

Glu Val Val Gly Asn Ile Ile Lys Cys Lys Thr Ala Lys Ser Arg Leu
                245                 250                 255

Thr Lys Glu Asn Ser Asp Val Lys Thr Arg Leu Tyr Tyr Asp Arg Gly
            260                 265                 270

Leu Asp Arg Tyr Tyr Gly Leu Leu Glu Leu Gly Glu Lys His Gly Val
        275                 280                 285

Phe Ser Arg Lys Gly Asn Arg Val Val Gly Asp Ser Ser Val Tyr
    290                 295                 300

Pro Ser Ala Ile Leu Ala Asp Pro Asp Lys Tyr Phe Thr Glu Glu Leu
305                 310                 315                 320

Met Glu Lys Leu Asp Glu Ala Ala Lys Glu Phe Arg Tyr Gly Asn
                325                 330                 335

<210> SEQ ID NO 32
<211> LENGTH: 343
<212> TYPE: PRT
<213> ORGANISM: Synechococcus phage S-PM2

<400> SEQUENCE: 32

Met Ser Phe Leu Asp Ser Val Ile Lys Asp Ser Lys Asn Glu Tyr Ala
1               5                   10                  15

Ala Phe Ala Ser Glu Gly Val Ala Gly Asp Val Glu Ser Phe Val
            20                  25                  30

Asp Thr Gly Ser Tyr Ile Phe Asn Ala Leu Val Ser Gly Ser Ile Phe
        35                  40                  45

Gly Gly Ile Pro Ser Asn Lys Ile Thr Ala Leu Ala Gly Glu Ser Gly
    50                  55                  60

Thr Gly Lys Thr Phe Phe Cys Leu Ser Val Val Arg Asn Phe Leu Asn
65                  70                  75                  80

Thr Asp Pro Asp Ala Gly Val Ile Tyr Phe Glu Thr Glu Ser Ala Ile
                85                  90                  95

Ser Lys Gln Met Ile Glu Ser Arg Gly Ile Asp Ser Thr Arg Met Ile
            100                 105                 110

Ile Phe Pro Val Asp Thr Ile Glu Asp Phe Arg Thr Gln Ala Val Arg
        115                 120                 125

Ile Ile Asp Lys Tyr Met Glu Gln Asn Lys Ser Glu Arg Lys Pro Leu
    130                 135                 140

Met Phe Val Leu Asp Ser Leu Gly Met Leu Ala Thr Lys Lys Glu Val
145                 150                 155                 160

Glu Asp Ala Ser Asn Asp Lys Gln Val Arg Asp Met Thr Lys Ala Gln
                165                 170                 175

Ile Val Lys Ser Ala Phe Arg Ile Leu Thr Leu Lys Met Gly Lys Ala
            180                 185                 190

Asn Ile Pro Met Leu Val Thr Asn His Thr Tyr Asp Val Val Gly Ser

```
                195                 200                 205
Tyr Val Pro Thr Lys Glu Met Gly Gly Gly Ser Gly Leu Lys Tyr Ser
    210                 215                 220

Ala Ser Thr Ile Val Tyr Leu Gly Lys Lys Glu Lys Asp Gly Thr
225                 230                 235                 240

Asp Leu Val Gly Asn Ile Ile Lys Cys Glu Ala Lys Lys Ser Arg Leu
                245                 250                 255

Thr Arg Glu Gly Ser Lys Val Lys Thr Arg Leu Phe Phe Asp Gln Arg
            260                 265                 270

Gly Leu Glu Arg Tyr Tyr Gly Met Leu Glu Leu Gly Glu Arg Ala Gly
        275                 280                 285

Leu Trp Lys Asn Thr Ala Gly Arg Tyr Glu Ile Asn Gly Lys Lys Val
    290                 295                 300

Tyr Gly Lys Gln Ile Leu Ala Asn Pro Asp Phe Phe Thr Glu Glu
305                 310                 315                 320

Ile Leu Gln Glu Leu Asp Lys Gln Ala Gln Arg Glu Phe Leu Tyr Gly
                325                 330                 335

Ala Ser Asp Asp Gly Glu Asp
            340

<210> SEQ ID NO 33
<211> LENGTH: 393
<212> TYPE: PRT
<213> ORGANISM: Enterobacteria phage RB32

<400> SEQUENCE: 33

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys His Phe Lys Ser Asn Met Ser Leu Thr Met Val Ala Ala Tyr Leu
65                  70                  75                  80

Asn Lys Tyr Pro Asp Ala Val Cys Leu Phe Tyr Asp Ser Glu Phe Gly
                85                  90                  95

Ile Thr Pro Ala Tyr Leu Arg Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Ala Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220
```

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
            245                 250                 255

Lys Phe Lys Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
            275                 280                 285

Asn Gly Trp Tyr Ala Arg Glu Phe Leu Asp Glu Thr Gly Glu Met
290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
            325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
            355                 360                 365

Glu Ser Lys Ser Lys Ser Ala Ala Asp Leu Thr Asp Leu Glu Gln
370                 375                 380

Leu Ser Asp Met Glu Glu Phe Asn Glu
385                 390

<210> SEQ ID NO 34
<211> LENGTH: 366
<212> TYPE: PRT
<213> ORGANISM: Vibrio phage nt-1

<400> SEQUENCE: 34

Met Ser Asp Leu Leu Lys Ser Leu Lys Lys Ser Ser Thr Ser Gly Tyr
1               5                   10                  15

Ala His Val Leu Ser Glu Ser Gln Phe Met Phe Glu Lys Asp His Thr
                20                  25                  30

Arg Thr Tyr Val Pro Ala Ile Asn Ile Ala Phe Ser Gly Glu Val Asp
            35                  40                  45

Gly Gly Leu Thr Ser Gly Leu Thr Val Leu Ala Gly Pro Ser Lys His
50                  55                  60

Phe Lys Ser Asn Leu Gly Leu Val Gly Val Ala Tyr Leu Lys Lys
65                  70                  75                  80

Tyr Pro Glu Ala Ile Cys Val Phe Ile Asp Thr Glu Phe Gly Ile Thr
                85                  90                  95

Pro Ser Tyr Leu Lys Ser Gln Gly Val Asp Pro Glu Arg Val Leu His
            100                 105                 110

Ile Gln Cys Glu Ser Val Glu Arg Met Lys Phe Glu Met Ala Asn Gln
        115                 120                 125

Leu Lys Asp Leu Ala Glu Arg Lys Arg Ala Lys Lys Ala Gly Glu Glu
130                 135                 140

Pro Asp Arg Val Val Phe Ile Asp Ser Val Gly Asn Val Ala Ser
145                 150                 155                 160

Ala Lys Glu Ile Asp Asp Ala Gln Asn Glu Lys Ser Val Ala Asp Met
                165                 170                 175

Ser Arg Ala Lys Gln Leu Lys Ser Leu Phe Arg Ile Ile Thr Pro Tyr
            180                 185                 190

Phe Thr Met Leu Asp Ile Pro Cys Ile Ala Ile Asn His Thr Tyr Gln
        195                 200                 205

Thr Gln Glu Met Tyr Ser Lys Thr Val Met Ser Gly Thr Gly Ile
    210                 215                 220

Met Tyr Ser Ala Asp Thr Val Ile Ile Leu Gly Lys Gln Gln Glu Lys
225                 230                 235                 240

Asp Gly Lys Glu Ile Ile Gly Tyr His Phe Ile Met Asn Ile Glu Lys
                245                 250                 255

Ser Arg Phe Val Lys Glu Lys Met Lys Val Lys Leu Thr Val Thr Tyr
            260                 265                 270

Glu His Gly Ile Asp Gln Phe Ser Gly Leu Leu Asp Ile Ala Leu Gln
        275                 280                 285

Thr Gly His Val Val Lys Pro Ser Asn Gly Trp Tyr Gln Arg Ala Phe
    290                 295                 300

Ile Asp Glu Glu Thr Gly Glu Ile Glu Ile Glu Glu Lys Lys Tyr Arg
305                 310                 315                 320

Ala Lys Glu Thr Gln Thr Leu Ser Phe Trp Lys Glu Ile Ile Asn Ser
                325                 330                 335

Pro Thr Phe Lys Thr Gly Val Lys Arg Leu Tyr Cys Leu Gly Gln Leu
            340                 345                 350

Asp Glu Ser Glu Leu Leu Asp Glu Val Asp Ser Leu Phe Asp
        355                 360                 365

<210> SEQ ID NO 35
<211> LENGTH: 381
<212> TYPE: PRT
<213> ORGANISM: Enterobacteria phage RB16

<400> SEQUENCE: 35

Met Ser Asn Lys Ala Leu Leu Lys Lys Leu Ile Lys Asn Ser Asn Ser
1               5                   10                  15

Gln Ser Ala Ser Ile Leu Ser Glu Ser Asp Val Phe Asn Asn Ile Thr
            20                  25                  30

Lys Thr Arg Thr Arg Val Pro Ile Leu Asn Leu Val Leu Ser Gly Ala
        35                  40                  45

Phe Asp Gly Gly Leu Thr Ser Gly Leu Thr Leu Ile Ala Gly Pro Ser
    50                  55                  60

Lys His Phe Lys Ser Asn Leu Gly Leu Val Ala Val Ala Ala Tyr Leu
65                  70                  75                  80

Lys Ala Asn Glu Asp Ala Val Cys Leu Phe Tyr Asp Ser Glu Lys Gly
                85                  90                  95

Val Thr Lys Ser Tyr Leu Lys Ser Met Gly Val Asp Pro Asp Arg Val
            100                 105                 110

Val Tyr Thr Arg Ile Thr Thr Val Glu Gln Leu Arg Asn Asp Val Val
        115                 120                 125

Ser Gln Leu Asp Ala Leu Glu Arg Gly Asp Lys Val Ile Ile Phe Val
    130                 135                 140

Asp Ser Val Gly Asn Thr Ala Ser Lys Lys Glu Leu Lys Asp Ala Leu
145                 150                 155                 160

Glu Asp Asn Asp Lys Gln Asp Met Thr Arg Ala Lys Ala Leu Lys Gly
                165                 170                 175

Met Phe Arg Met Val Thr Pro Tyr Leu Ala Asp Ile Asp Ile Pro Met
            180                 185                 190

Val Cys Ile Cys His Thr Tyr Asp Thr Gln Glu Met Tyr Ser Lys Lys
        195                 200                 205

Val Ile Ser Gly Gly Thr Gly Leu Met Tyr Ser Ala Asp Thr Ala Ile

```
                210                 215                 220
Ile Leu Gly Lys Gln Gln Val Lys Glu Gly Thr Glu Val Val Gly Tyr
225                 230                 235                 240

Asp Phe Ile Met Asn Val Glu Lys Ser Arg Phe Val Lys Glu Lys Ser
                245                 250                 255

Lys Phe Lys Leu His Val Thr Tyr Glu Gly Ile Ser Met Phe Ser
                260                 265                 270

Gly Leu Leu Asp Leu Ala Met Glu Met Asn Phe Val Gln Thr Pro Thr
                275                 280                 285

Lys Gly Trp Arg Gly Arg Ala Phe Leu Asn Thr Glu Thr Gly Glu Leu
                290                 295                 300

Glu Leu Glu Glu Lys Lys Trp Arg Glu Ala Glu Thr Asn Cys Ile Glu
305                 310                 315                 320

Phe Trp Lys Pro Leu Phe Lys His Gln Pro Phe Ile Asp Ala Ile Gln
                325                 330                 335

Asp Lys Tyr Arg Ile Pro Asp Lys Glu Ile Thr Asp Gly Ala Ala Leu
                340                 345                 350

Glu Asp Leu Tyr Ser Asp Asp Val Val Glu Ser Asn Lys Val Asp Phe
                355                 360                 365

Asp Asp Asp Ile Pro Asp Asp Val Asp Leu Met Glu Glu
                370                 375                 380

<210> SEQ ID NO 36
<211> LENGTH: 9
<212> TYPE: PRT
<213> ORGANISM: Artificial Sequence
<220> FEATURE:
<223> OTHER INFORMATION: Semi Conserved Domain

<400> SEQUENCE: 36

Phe Arg Asp Ala Ile Lys Arg Ala Tyr
1               5
```